United States Patent
Mitchell et al.

(10) Patent No.: US 11,464,805 B2
(45) Date of Patent: Oct. 11, 2022

(54) CCR2+ HEMATOPOIETIC STEM CELLS MEDIATE T CELL ACTIVATION IN ADOPTIVE CELL THERAPY

(71) Applicant: University of Florida Research Foundation, Incorporated, Gainesville, FL (US)

(72) Inventors: Duane Mitchell, Gainesville, FL (US); Catherine Flores, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 464 days.

(21) Appl. No.: 16/472,618

(22) PCT Filed: Dec. 21, 2017

(86) PCT No.: PCT/US2017/067914
§ 371 (c)(1),
(2) Date: Jun. 21, 2019

(87) PCT Pub. No.: WO2018/119243
PCT Pub. Date: Jun. 28, 2018

(65) Prior Publication Data
US 2021/0283184 A1 Sep. 16, 2021

Related U.S. Application Data

(60) Provisional application No. 62/437,582, filed on Dec. 21, 2016.

(51) Int. Cl.
*A61K 35/28* (2015.01)
*A61K 35/17* (2015.01)

(52) U.S. Cl.
CPC .............. *A61K 35/28* (2013.01); *A61K 35/17* (2013.01)

(58) Field of Classification Search
CPC .................................................... A61K 35/28
See application file for complete search history.

(56) References Cited

U.S. PATENT DOCUMENTS

2020/0332256 A1* 10/2020 Rahman ......... A61K 39/001192

FOREIGN PATENT DOCUMENTS

| WO | WO 2016/011210 A2 | 1/2016 |
| WO | WO 2017/023753 A1 | 2/2017 |

OTHER PUBLICATIONS

International Search Report and Written Opinion dated Mar. 5, 2018 for Application No. PCT/US2017/067914.
International Preliminary Report on Patentability dated Jul. 4, 2019 for Application No. PCT/US2017/067914.
Extended European Search Report dated May 4, 2020 for EP Patent Application No. 17885383.4.
Bouchlaka et al., Immunotherapy following hematopoietic stem cell transplantation: potential for synergistic effects. Immunotherapy. May 2010;2(3):399-418. doi: 10.2217/imt.10.20.
Clarkson et al., CCR2-dependent dendritic cell accumulation in the central nervous system during early effector experimental autoimmune encephalomyelitis is essential for effector T cell restimulation in situ and disease progression. J Immunol. Jan. 15, 2015;194(2):531-41. doi: 10.4049/jimmunol.1401320. Epub Dec. 10, 2014.
Flores et al., Novel role of hematopoietic stem cells in immunologic rejection of malignant gliomas. Oncoimmunology. Jan. 22, 2015;4(3):e994374. eCollection Mar. 2015.
Goodrich et al., Altered neural cell fates and medulloblastoma in mouse patched mutants. Science. Aug. 22, 1997;277(5329):1109-13.
Moon et al., Expression of a functional CCR2 receptor enhances tumor localization and tumor eradication by retargeted human T cells expressing a mesothelin-specific chimeric antibody receptor. Clin Cancer Res. Jul. 15, 2011;17(14):4719-30. doi: 10.1158/1078-0432.CCR-11-0351. Epub May 24, 2011.
Perica et al., Adoptive T cell immunotherapy for cancer. Rambam Maimonides Med J. Jan. 29, 2015;6(1):e0004. doi: 10.5041/RMMJ.10179. eCollection Jan. 2015.
Pham et al., Differential Immune Microenvironments and Response to Immune Checkpoint Blockade among Molecular Subtypes of Murine Medulloblastoma. Clin Cancer Res. Feb. 1, 2016;22(3):582-95. doi: 10.1158/1078-0432.CCR-15-0713. Epub Sep. 24, 2015.
Reilly et al., Nf1;Trp53 mutant mice develop glioblastoma with evidence of strain-specific effects. Nat Genet. Sep. 2000;26(1):109-13.
Rosenberg, Raising the bar: the curative potential of human cancer immunotherapy. Sci Transl Med. Mar. 28, 2012;4(127):127ps8. doi: 10.1126/scitranslmed.3003634. Review.
Rosenberg, Cell transfer immunotherapy for metastatic solid cancer—what clinicians need to know. Nat Rev Clin Oncol. Aug. 2, 2011;8(10):577-85. doi: 10.1038/nrclinonc.2011.116. Review.
Sagar et al., Dendritic cell CNS recruitment correlates with disease severity in EAE via CCL2 chemotaxis at the blood-brain barrier through paracellular transmigration and ERK activation. J Neuroinflammation. Oct. 26, 2012;9:245. doi: 10.1186/1742-2094-9-245.
Si et al., CCR2 mediates hematopoietic stem and progenitor cell trafficking to sites of inflammation in mice. J Clin Invest. Apr. 2010;120(4):1192-203. doi: 10.1172/JCI40310. Epub Mar. 15, 2010.
Wrzesinski et al., Hematopoietic stem cells promote the expansion and function of adoptively transferred antitumor CD8 T cells. J Clin Invest. Feb. 2007;117(2):492-501.

* cited by examiner

*Primary Examiner* — Scott Long
(74) *Attorney, Agent, or Firm* — Wolf, Greenfield & Sacks, P.C.

(57) ABSTRACT

The combination of adoptive cell therapy with CCR2 positive (CCR2$^+$) hematopoietic stem cell transplantation increases T cell activation and survival.

20 Claims, 15 Drawing Sheets

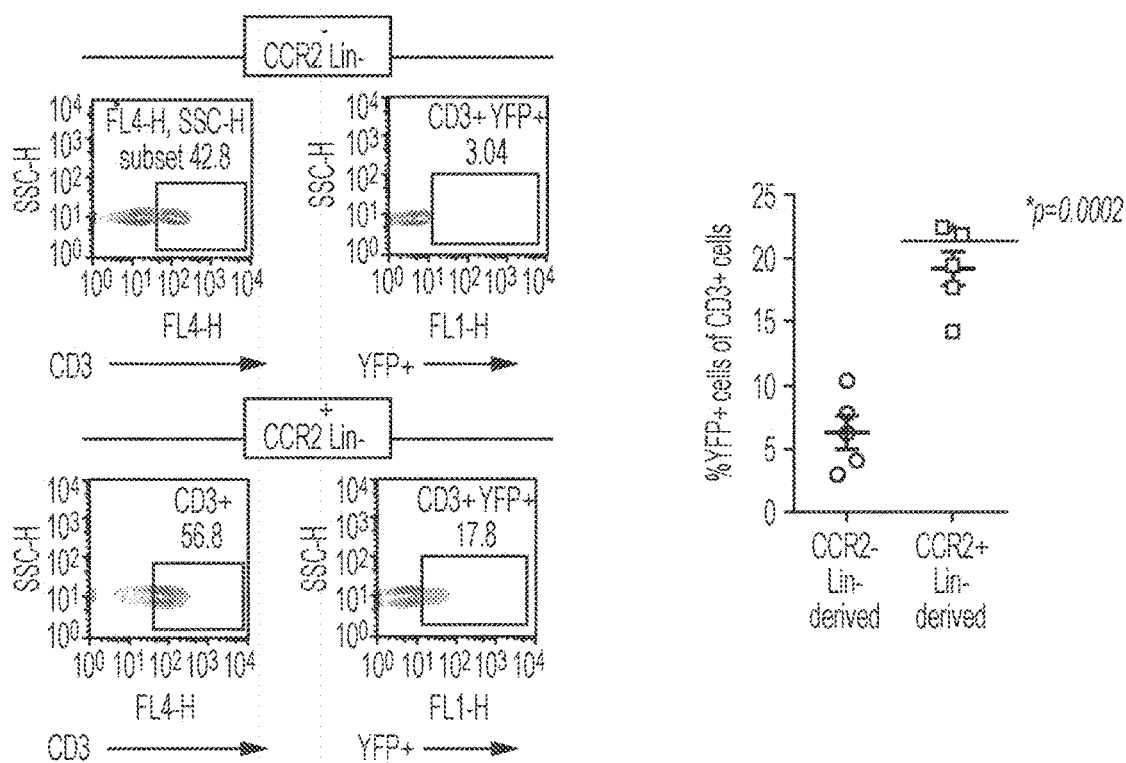
Figure 3A
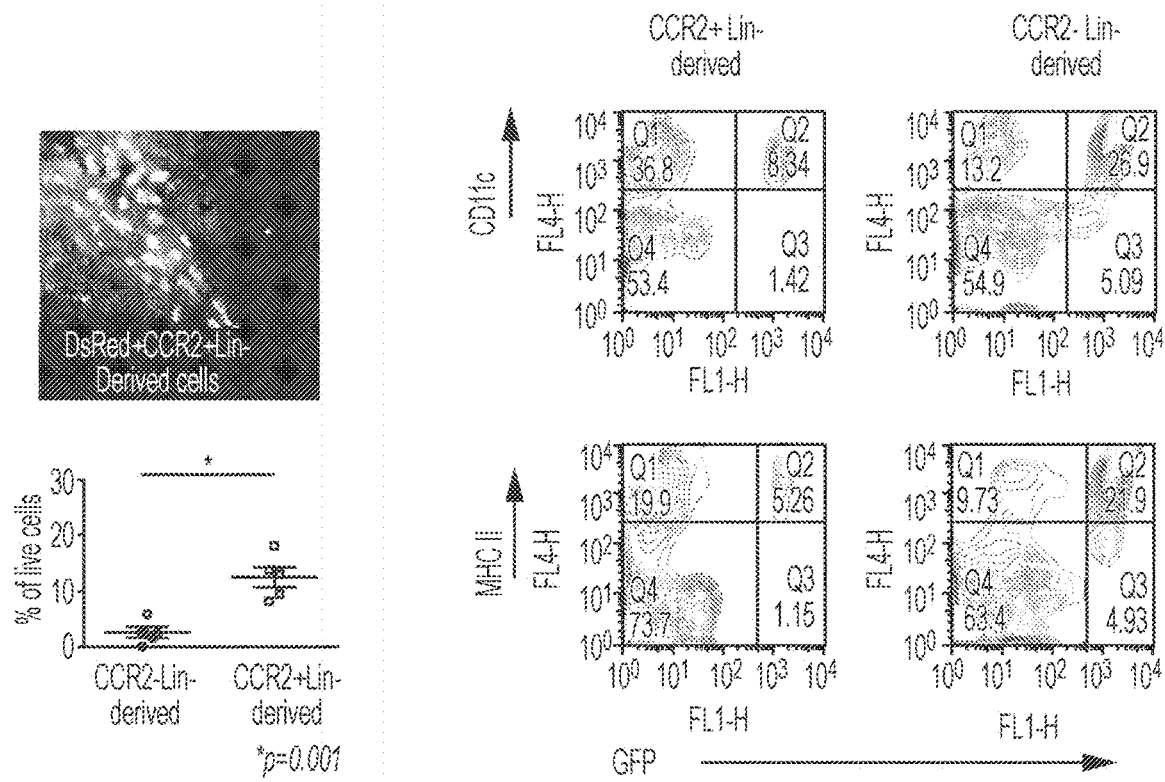
Figure 3B
Figure 3C

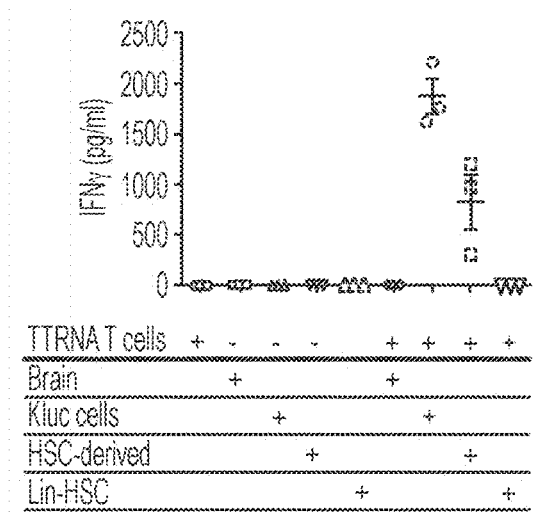
Figure 5A
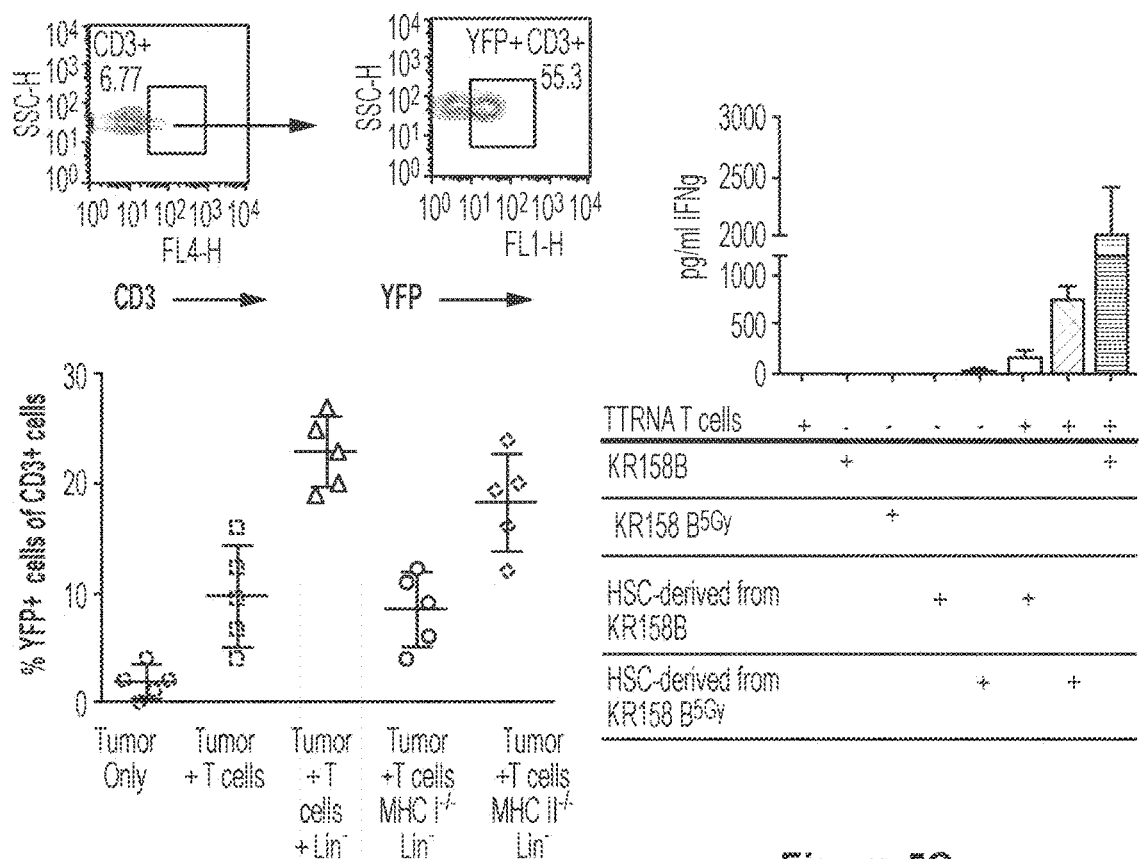
Figure 5B
Figure 5C

CCR2+ HEMATOPOIETIC STEM CELLS MEDIATE T CELL ACTIVATION IN ADOPTIVE CELL THERAPY

RELATED APPLICATIONS

This application is a national stage filing under 35 U.S.C. § 371 of International Patent Application Serial No. PCT/US2017/067914, filed Dec. 21, 2017, which claims the benefit under 35 U.S.C § 119(e) of U.S. provisional application No. 62/437,582, filed Dec. 21, 2016, each of which is incorporated herein by reference in its entirety.

GOVERNMENT SUPPORT

This invention was made with government support under grant number R01 CA195563, awarded by the National Institutes of Health. The government has certain rights in the invention.

BACKGROUND OF THE DISCLOSURE

Enhancing CD4 and CD8 T cell activity against a variety of cells, including cancer cells, is an approach being investigated to treat cancers and infectious diseases. In one strategy, T lymphocytes are stimulated with antigen, expanded ex vivo, and then transfused into a subject. This is a form of adoptive cellular therapy (ACT). Certain ACT strategies have been shown in early stage clinical trials to induce cancer regression. ACT may be particularly useful in treating cancers and/or infectious diseases that arise following immune-ablation and hematopoietic stem cell transplantation (HSCT).

Another approach being investigated for treating cancer is high-dose chemotherapy followed by hematopoietic stem cell transplantation (HSCT) using hematopoietic stem cells (HSCs) collected from bone marrow or mobilized from the marrow and collected in the peripheral blood. HSCT and/or HSC mobilization, when combined with treatments to induce lymphopenia, may enhance the effects of certain cell-based immunotherapies. The administration of HSCs or an HSC mobilizing agent alone does not show clinical effects in many subjects with different cancers.

The inventors previously made the unique observation that bone marrow derived-hematopoietic stem cells (HSCs), including CCR2+ cells, can enhance immune checkpoint inhibitor therapy in certain instances (PCT/US16/44718, the entirety of which is incorporated by reference herein).

SUMMARY OF THE DISCLOSURE

It has been discovered according to the present disclosure that administration of CCR2 positive (CCR2$^+$) HSCs with ACT significantly increases activation and IFNγ secretion of adoptively transferred T cells within the tumor microenvironment and in tumor draining lymph nodes relative to ACT alone. The inventors have surprisingly found that the administration of CCR2$^+$ HSCs to a subject receiving adoptive cell therapy (ACT) but not receiving immune checkpoint blockade with an immune checkpoint inhibitor results in increased survival of ACT. Without wishing to be bound by any theory of the disclosure, insight into mechanism is provided through demonstration that the combination of CCR2$^+$HSC transfer with ACT leads to an increase in IFNγ positive T cells within the tumor microenvironment.

In one aspect, the ACT platform employs bone marrow-derived dendritic cells pulsed with total RNA from tumor to expand tumor-specific T cells (TTRNA-T cells) ex vivo (Flores et al., 2015). These studies demonstrate that HSC administration with ACT significantly increases TTRNA-T cell activation and IFNγ secretion within the tumor microenvironment and in tumor draining lymph nodes relative to ACT alone. According to the present invention, a method of treating a disease selected from cancer or an infectious disease in a subject is provided. The method involves administering to the subject having the disease adoptive cell therapy (ACT) and administering to the subject a preparation containing hematopoietic stem cells, in amounts effective to treat the disease, wherein the hematopoietic stem cells (HSCs) are enriched for CCR2 positive (CCR2+) cells (or precursors of CCR2+ cells), and wherein the subject is not receiving an immune checkpoint inhibitor.

In embodiments, the HSCs in the preparation are lineage depleted. In embodiments, the HSCs in the preparation are at least 10%, 20%, 30%, 40%, 50%, 60%, 70%, 80%, 90%, 95%, 98% or even 99% CCR2+ cells (or precursors of CCR2+ cells). In embodiments, the HSCs in the preparation are less than 50%, 40%, 30%, 20%, 10%, 5%, 2%, or even less than 1% CCR2 negative (CCR2−) cells. In embodiments, between 50% and 100% of the cells in the preparation are CCR2+ cells (or precursors of CCR2+ cells).

In embodiments, the cells in the preparation are precursors of CCR2+ cells as defined as CD34+HSCs, CD34+CD38+ HSCs, or aldehyde dehydrogenase (ALDH) bright HSCs that can give rise to CCR2+ lineage negative HSCs.

In any of the forgoing embodiments, optionally the subject has been treated with radiation therapy or chemotherapy. In any of the foregoing embodiments, optionally the subject is scheduled to receive radiation therapy or chemotherapy.

In any of the forgoing embodiments, the source of hematopoietic stem cells may be bone marrow, peripheral blood, umbilical cord blood, or induced pluripotent stem cells. In any of the forgoing embodiments, the source of hematopoietic stem cells may be hematopoietic progenitor cells. In any of the forgoing embodiments, the source of stem cells may be autologous. In any of the forgoing embodiments, the source of stem cells may be allogeneic and the donor cells are HLA-matched to the recipient.

In any of the forgoing embodiments, the adoptive cell therapy may be chimeric antibody receptor (CAR)-modified T cells. In some embodiments, the therapy can be used to treat any of the diseases or infections described herein. In any of the forgoing embodiments, the disease can be cancer and the cancer may be melanoma, squamous cell carcinoma, basal cell carcinoma, breast cancer, head and neck carcinoma, thyroid carcinoma, soft tissue sarcoma, bone sarcoma, testicular cancer, prostatic cancer, ovarian cancer, bladder cancer, skin cancer, brain cancer, glioblastoma, medulloblastoma, ependymoma, angiosarcoma, hemangiosarcoma, mast cell tumor, primary hepatic cancer, small cell lung cancer, non-small-cell lung cancer, pancreatic cancer, gastrointestinal cancer, renal cell carcinoma, hematopoietic neoplasia, lymphoma, mesothelioma, glioblastoma, low-grade glioma, high-grade glioma, pediatric brain cancer, medulloblastoma, or a metastatic cancer thereof.

In embodiments, the cancer is a metastatic or refractory cancer of the brain, lung, breast, or melanoma. En embodiments, the cancer is a metastatic brain cancer from non-small cell lung cancer, a metastatic brain cancer from melanoma, or a metastatic brain cancer from breast carcinoma. In embodiments, the cancer is glioblastoma, low-grade glioma, high-grade glioma, pediatric brain cancer, or medulloblastoma.

In any of the forgoing embodiments, the disease can be an infectious disease. In embodiments, the infectious disease is a chronic infectious disease. In embodiments, the infectious disease is any hepatitis, adenovirus, polyoma virus such as BK, human immunodeficiency virus (WV), herpes simplex virus (HSY), respiratory syncytial virus (RSV), cytomegalovirus (CMV), Epstein-Barr vims (EBY), Influenza A, B, and/or C, vesicular stomatitis virus (VSV), vesicular stomatitis vims (VSV), Staphylococcus species including Methicillin-resistant *Staphylococcus aureus* (MRSA), *Streptococcus* species including *Streptococcus pneumonia*, or a post-transplant infection. In embodiments, the infectious disease is Hepatitis A, Hepatitis B, or Hepatitis C.

According to another aspect of the invention, an improvement to ACT to treat a subject is provided. The improvement involves administering to the subject a preparation containing hematopoietic stem cells (i.e., administering HST), wherein the hematopoietic stem cells (HSCs) are enriched for CCR2 positive (CCR2+) cells (or precursors of CCR2+ cells), and wherein the subject is not receiving an immune checkpoint inhibitor. In embodiments, the HSCs in the preparation are lineage depleted. In embodiments, the HSCs in the preparation are at least 10%, 20%, 30%, 40%, 50%, 60%, 70%, 80%, 90%, 95%, 98% or even 99% CCR2+ cells (or precursors of CCR2+ cells). In embodiments, the HSCs in the preparation are less than 50%, 40%, 30%, 20%, 10%, 5%, 2%, or even less than 1% CCR2 negative (CCR2−) cells. In embodiments, between 50% and 100% of the cells in the preparation are CCR2+ cells (or precursors of CCR2+ cells). In any of the foregoing embodiments, the ACT may be to treat a subject with cancer or with an infectious disease. The cancers and infectious diseases may be as described above.

According to another aspect of the invention, a kit is provided. The kit is a package containing a first vessel containing T Cells for ACT and a second vessel containing HSCs, wherein the hematopoietic stem cells (HSCs) are enriched for CCR2 positive (CCR2+) cells (or precursors of CCR2+ cells), and instruction for use wherein the instructions indicate use without an immune checkpoint inhibitor. In embodiments, the HSCs in the preparation are lineage depleted. In embodiments, the HSCs in the preparation are at least 10%, 20%, 30%, 40%, 50%, 60%, 70%, 80%, 90%, 95%, 98% or even 99% CCR2+ cells (or precursors of CCR2+ cells). In embodiments, the HSCs in the preparation are less than 50%, 40%, 30%, 20%, 10%, 5%, 2%, or even less than 1% CCR2 negative (CCR2−) cells. In embodiments, between 50% and 100% of the cells in the preparation are CCR2+ cells (or precursors of CCR2+ cells). In any of the foregoing embodiments, the T cells and the HSCs may be, or may not be, syngeneic). In any of the foregoing embodiments, the T cells may be CarT cells. In any of the foregoing embodiments, the T cells and the HSCs may be HLA matched. These and other aspects of the invention are described in further detail below.

BRIEF DESCRIPTION OF THE DRAWINGS

FIGS. 3A-3C show that CCR2+ HSC transfer is associated with increased TTRNA-T cell activation within tumor microenvironment. FIG. 3A shows HSCs were further isolated into CCR2+HSC or CCR2-HSC and transferred into tumor bearing mice that received ACT. Tumor-specific T cells for ACT were generated using GREAT mice. One week post-ACT, tumors were harvested and relative expression of YFP (IFNγ) was quantified between groups. FIG. 3B shows that 24 hrs post transfer, more CCR2+HSCs are found in intracranial tumor relative to CCR2−HSCs. FIG. 3C shows CCR2−HSC-derived cells and CCR2+HSC-derived cells were isolated from intracranial tumors of mice that received ACT with either CCR2−HSCs or CCR2+HSCs. HSC-derived cells were phenotyped using flow cytometry.

FIGS. 5A-5C show that CCR2+ HSC-derived cells present tumor antigens to T cells within intracranial tumor. FIG. 5A shows HSC-derived cells were isolated from tumor bearing mice that received. ACT. Effector tumor-specific T cells (TTRNA T cells) were used in an in vitro functionality assay to target the isolated HSC-derived cells. IFNγ secretion was measured as an indication that cognate tumor antigen was being presented to tumor-specific T cells (TTRNA T cells). FIG. 5B shows IISCs isolated from either MHC I$^{-/-}$ or MHC II$^{-/-}$ mice were transferred into late tumor bearing mice that received ACT with tumor-specific T cells generated from GREAT mice, One week post-ACT, tumors were excised and analyzed for relative expression of CD3$^+$YFP$^+$ cells. FIG. 5C shows that HSC-derived cells isolated from intracranial tumor with or without irradiation has the capacity to activate TTRNA-T cells.

FIG. 6A shows mice bearing established KR158B intracranial glioma received adoptive cell therapy plus either GFP$^+$ HSCs, GFP$^+$CCR2$^-$HSCs, or GFP$^+$CCR2$^+$HSCs. One week post-ACT, GFP+ cells were isolated from tumors using sterile FACS. These were then used as a "vaccine" for a second set of tumor bearing mice that received ACT using DsRed$^+$ tumor-specific T cells, FIG. 6B shows vaccine draining lymph nodes were collected one week after "vaccine", and relative expansion of DsRed+ tumor-specific T cells between groups was assessed using flow cytometry.

DETAILED DESCRIPTION

Figure 1A:
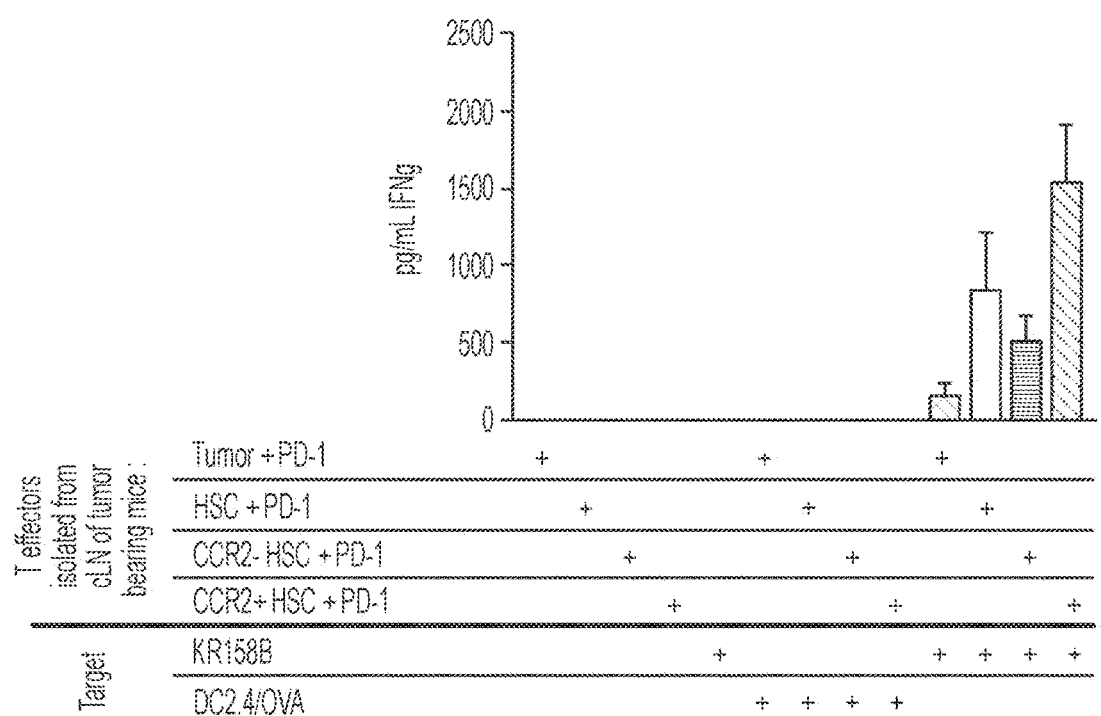
FIG. 1A shows that CCR2+HSCs can cross prime host T cells in draining lymph nodes when combined with anti-PD-1 in a malignant glioblastoma model.

The following detailed description is made by way of illustration of certain aspects of the disclosure. It is to be understood that other aspects are contemplated and may be made without departing from the scope or spirit of the present disclosure. The following detailed description, including the Examples, therefore, is not to be taken in a limiting sense. Scientific and technical terms used herein have meanings commonly used in the art unless otherwise specified. The definitions provided herein are to facilitate understanding of certain terms used frequently herein and are not meant to limit the scope of the present disclosure. The singular forms "a", "an", and "the" encompass the plural, unless the content clearly dictates otherwise. The term "or" is generally employed in its sense including "and/or" unless the content clearly dictates otherwise.

Adoptive Cell Therapy (ACT or adoptive cell transfer). Adoptive cell therapy is the transfer of cells into a patient for the purpose of transferring immune functionality and other characteristics with the cells. The cells are most commonly immune-derived, for example T cells, and can be autologous or allogeneic. If allogenic, they are typically HLA matched. Generally, in cancer immunotherapy, T cells are extracted from the patient, optionally genetically modified, and cultured in vitro and returned to the same patient. Transfer of autologous cells rather than allogeneic cells minimizes graft versus host disease issues. Transfer of allogeneic cells rather than autologous cells maximizes flexibility in preparation and storage of T cells, for example. Ideally, there can be used so-called universal donor cells. ACT can be used for treatment of viral infections and/or cancer.

The use of allogeneic ACT in a subject in the period following immuno-suppression is thought to be advantageous to the subject, with the potential for enhancing immunity, including antitumor immunity, and increasing vaccine efficacy in the period following immunosuppression. ACT of tumor-specific T cells has been shown to be effective in treatment of solid tumors in murine and in human systems. In embodiments of the disclosure, ACT is used with $CCR2^+$ HSC infusion, wherein the addition of $CCR2^+$ HSCs increases the immune capability of the subject relative to ACT alone.

Chimeric Antigen Receptor (CAR) Modified T Cells (CARTs)

In some embodiments, the T cells transferred with ACT are CARTs. Chimeric antigen receptor (CAR) modified T cells (CARTs) have great potential in selectively targeting specific cell types, and utilizing the immune system surveillance capacity and potent self-expanding cytotoxic mechanisms against tumor cells with exquisite specificity. This technology provides a method to target neoplastic cells with the specificity of monoclonal antibody variable region fragments, and to affect cell death with the cytotoxicity of effector T cell function. For example, the antigen receptor can be a scFv or any other monoclonal antibody domain. In some embodiments, the antigen receptor can also be any ligand that binds to the target cell, for example, the binding domain of a protein that naturally associates with cell membrane proteins.

CART therapy has been successfully applied for the treatment of several different tumor types, which had been refractory to other forms of treatment. A key to CART therapy is the availability of cell surface antigens that can be targeted in a cell specific manner There are several cell surface antigens that are selectively expressed In some embodiments, the present invention relates, in part, to the use of T cells genetically modified to express a desired CAR, (e.g., containing a IL-15Rα cytoplasmic domain). T cells expressing a CAR are referred to herein as CAR T cells, CARTs, or CAR modified. T cells. Preferably, the cell can be genetically modified to express an antibody binding domain on its surface, conferring novel antigen specificity that is MHC independent. In some instances, the T cell is genetically modified to express a CAR that combines an antigen recognition domain of a specific antibody with a transmembrane domain and a cytoplasmic domain into a single chimeric protein. In some embodiments, two CAR proteins dimerize (e.g., form homo- or heterodimers) in vivo.

Hematopoietic Stem Cell. A hematopoietic stem cell (HSC), also called a blood stem cell, is an immature cell found in the blood and the bone marrow that can renew itself, and that can differentiate into a variety of specialized cells, such as blood and immune cells, including white blood cells, red blood cells, and platelets. HSCs can mobilize out of the bone marrow into circulating blood. HSCs facilitate constant renewal of blood cells, producing billions of new blood cells each day.

Hematopoietic Stem Cell Transplantation (HSCT). Hematopoietic stem cell (HSC) transplantation (HSCT or HSC transfer) is the transplantation of HSCs, usually derived from peripheral blood, bone marrow, or umbilical cord blood. Two types of HSCT may be used in a subject: autologous stem cell transplantation, wherein the subject's own stem cells are used, or allogenic stem cell transplantation, wherein a donor's stem cells, that are genetically similar and HLA-matched to the recipient, are transplanted into the subject. In some embodiments of the disclosure, autologous stem cells are used for HSCT. In some embodiments of the disclosure, allogeneic stem cells that are HLA-matched to the subject are used for HSCT. In some embodiments, in autologous HSCT, a sample containing stem cells are removed from the subject, stored, and later transplanted back into the subject. In some embodiments, in allogeneic or autologous HSCT, a sample containing CCR2+ stem cells are removed from the subject, stored, and later transplanted into the subject. In some embodiments, in allogeneic or autologous HSCT, a sample containing CCR2+ stem cells are removed from the subject, expanded in culture ex vivo, and later transplanted into the subject. In some embodiments, in allogeneic or autologous HSCT, a sample containing CCR2+ stem cells are removed from the subject, the sample is selected for CCR2+ cells, the selected cells are then expanded in culture ex vivo. In some embodiments, the expanded/cultured cells are again selected for CCR2+ cells. In some embodiments, the CCR2+ selected cells are stored. In some embodiments, the CCR2+ selected cells are transplanted into the subject. The CCR2+ selected cells are transplanted into a subject receiving ACT. In some embodiments, the subject also receives irradiation or chemotherapy.

Hematopoietic stem cells (HSC) and subsets thereof. HSCs represent a small fraction of the total population of blood cells in the sample, so it may be advantageous to increase the number of autologous or allogeneic HSCs before administering CCR2+ stem cells to a subject for treatment of a disease in the subject such as cancer or infectious disease. In some embodiments of the disclosure, hematopoietic stem cells are collected and expanded, before transplanting them into the subject for treatment. In some embodiments of the disclosure, hematopoietic stem cells are collected, expanded, and selected for from the sample, before transplanting them into the subject for treatment. In some embodiments, a sample containing the hematopoietic stem cells is obtained and processed to expand the number of stem cells within the sample, in vitro, prior to administering to the subject the hematopoietic stem cells. In some embodiments, a sample containing the hematopoietic stem cells is obtained and processed to increase the percentage of stem cells within the sample, in vitro, prior to administering to the subject the hematopoietic stem cells.

According to the invention, hematopoietic stem cells or progenitors thereof are enriched in CCR2+ cells. In embodiments, the enrichment can occur by selectively stimulating the growth/expansion of stem cells versus other cells collected from a subject. In another embodiment, the stem cells can be enriched by isolating stem cells from other cells collected from a subject. Such selection may be so-called positive selection or negative selection. In some embodiments, a sample containing the hematopoietic stem cells is obtained and processed to expand the number of stem cells within the sample, in vitro, prior to administering to the subject the hematopoietic stem cells. In some embodiments, a sample containing the hematopoietic stem cells is obtained and processed to expand the number of CCR2+ stem cells or progenitors thereof within the sample, in vitro, prior to administering to the subject the hematopoietic stem cells. In some embodiments, the sample that was processed to expand the number of CCR2+ stem cells or progenitors thereof is depleted of CCR2− cells prior to administering to the subject the hematopoietic stem cells.

It is to be understood that HSCs isolated or selected for the CCR2$^+$ marker or progenitor cells thereof may additionally or alternatively be isolated by positive selection of CD34$^+$ or lin-cells. It is also to be understood that that HSCs isolated or selected for the CCR2$^+$ marker or progenitor cells thereof may additionally or alternatively be isolated by negative selection and removal of CCR2− cells, In some embodiments, CCR2$^+$ HSCs or progenitors thereof are isolated and expanded before administering the CCR2$^+$ HSCs to the subject. In some embodiments, HSCs are isolated, selected for CCR2$^+$ cells or progenitors thereof ex vivo, and expanded ex vivo before administering the CCR2$^+$ HSCs to the subject.

In positive selection, stem cells are isolated based on markers known to be on stem cells but not on other cells. In some embodiments, in positive selection, stem cells are isolated based on the markers CCR2$^+$, CD34$^+$, and/or lin-, thereby enriching the HSCs for the positive marker(s). In embodiments, stem cells are isolated based on the marker CCR2$^+$.

In negative selection, cells that are not stem cells are identified and removed based on markers on such other cells, leaving behind stem cells. In the negative selection, the HSCs can be processed ex vivo to deplete other than CCR2$^+$, CD34$^+$, and/or lin-cells.

Such selection procedures are well known to those of ordinary skill in the art and include but are not limited to flow cytometric analysis, microbead-based isolation, magnetic bead separation, adherence assays, and/or ligand-based selection. In some embodiments, the ligand-based selection is based on the presence of a CCR2 ligand, CCL2, CCL7, or CCL13.

In some embodiments, less than 50% of starting population of CCR2− HSCs remains. In some embodiments, less than 40%, 30%, 20%, 15%, 10%, 5%, 2% and even less than 1% of starting population of CCR2− HSCs remain. In some embodiments, a preparation of HSCs for administration contains no more than 1%, 2%, 3%, 4%, 5%, 6%, 7%, 8%, 9%, or 10% CCR2− HSCs.

In some embodiments, multiple steps of positive selection with intervening steps of proliferation can be used. In embodiments, the preparation for administration contain at least about 10%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% CCR2$^+$ cells, which also may be CD34$^+$, and/or lin-HSCs.

Sources of hematopoietic stem cells herein include: bone marrow lineage depleted cells (lin-), cKit$^+$ purified lineage negative bone marrow derived cells, Sca$^+$ purified lineage negative bone marrow derived cells, cKit$^+$Sca$^+$ purified bone marrow derived cells, mobilized from host bone marrow using G-CSF, mobilized from host bone marrow using AMD3100, Plerixafor, or the molecule 1,1'-[1,4-phenylenebis(methylene)]bis[1,4,8,11-tetraazacyclotetradecane], umbilical cord blood or cord-blood derived stem cells, human leukocyte antigen (HLA)-matched blood, mesenchymal stem cells derived from blood or marrow, hematopoietic stem cells differentiated from induced pluripotent stem cells, mobilized peripheral blood, peripheral blood, hematopoietic stem cell subsets including Lin-cells purified with CCR2$^+$ marker, lineage negative purified peripheral blood, or CD34$^+$ enriched peripheral blood. In some embodiments of the disclosure, the source of HSCs is bone marrow. In some embodiments of the disclosure, the source of HSCs is autologous or allogeneic, optionally wherein, the source is bone marrow, peripheral blood, umbilical cord blood, or induced pluripotent stem cells.

Hematopoietic Stem Cell Mobilizing Agent. In some embodiments of the disclosure, a hematopoietic stem cell mobilizing agent can be administered to the subject to aid in isolation of HSCs from the subject. HSC mobilization refers to the recruitment of HSCs from the bone marrow of a subject into the peripheral blood of the subject. In the current application, HSC mobilizing agents include: granulocyte colony-stimulating factor (G-CSF), PEGylated G-CSF (pegfilgratism), lenogratism, a glycosylated form of G-CSF, C-X-C motif chemokine 2 (CXCL2), C-X-C chemokine receptor type 4 (CXCR-4), and plerixafor.

Radiation Therapy or Chemotherapy. HSCT is often administered with chemotherapy. The inventors show herein (e.g., FIG. 7B) that the effects of combinatorial treatment of ACT and administration of CCR2$^+$ HSCs are enhanced with radiation therapy. In some embodiments, the subject receiving ACT and CCR2$^+$ HSCs also receives radiation therapy or chemotherapy.

Cancer. The therapies described herein include treatment of an existing or established cancer, that is, one that exists and is detectable in the subject. Additionally, treatment of a precancerous lesion (e.g., adenomatous polyp, or cellular dysplasia) for the prevention of the development of cancer is envisioned. Cancers treatable according to the current disclosure include the following cancers: melanoma, squamous cell carcinoma, basal cell carcinoma, breast cancer, head and neck carcinoma, thyroid carcinoma, soft tissue sarcoma, bone sarcoma, testicular cancer, prostatic cancer, ovarian cancer, bladder cancer, skin cancer, brain cancer, glioblastoma, medulloblastoma, ependymoma, angiosarcoma, hemangiosarcoma, mast cell tumor, primary hepatic cancer, small cell lung cancer, non-small-cell lung cancer, pancreatic cancer, gastrointestinal cancer, renal cell carcinoma, hematopoietic neoplasia, lymphoma, mesothelioma, or a metastatic cancer thereof. In embodiments of the disclosure, the cancers to be treated in the disclosure include glioblastoma, low-grade glioma, high-grade glioma, brain stem glioma, cortical glioblastoma, pediatric brain cancer, and medulloblastoma. In embodiments of the disclosure, the cancer is invasive intracranial glioma. In embodiments of the disclosure, the cancer is a metastatic or refractory cancer of the brain, lung, breast, or melanoma.

Infectious Disease. The disclosure also is useful in connection with the treatment of infectious disease. In general, opportunistic pathogenic microorganism may be categorized as virus, fungus, parasite, and bacterium. Illustrative pathogenic viral organisms causing human diseases include (but are not restricted to) Filoviruses, Herpes viruses, Hepatitis viruses, Retroviruses, Human Immunodeficiency Virus (HIV), orthomyxoviruses, Paramyxoviruses, Togaviruses, Picornaviruses, Papovaviruses and Gastroenteritisviruses. Illustrative pathogenic bacteria causing serious human diseases are the Gram positive organisms: *Staphylococcus aureus, Staphylococcus epidermidis, Enterococcus faecalis* and *E. faecium, Streptococcus pneumoniae* and the Gram negative organisms: *Pseudomonas aeruginosa, Burkholdia cepacia, Xanthomonas maltophila, Escherichia coli, Enterobacter* spp., *Klebsiella pneumoniae* and *Salmonella* spp. Illustrative pathogenic protozoan organisms causing human diseases include (but are not restricted to) Malaria e.g., *Plasmodium falciparum* and *M. ovale, Trypanosomiasis* (sleeping sickness) e.g., *Trypanosoma cruzei, Leischmaniasis* e.g., *Leischmania donovani, Amebiasis* e.g., *Entamoeba histolytica*. Illustrative pathogenic fungi causing or associated with human diseases include (but are not restricted to) *Candida albicans, Histoplasma neoforinans, Coccidioides immitis* and *Penicillium marneffei*. In embodiments, the infectious disease organism is one involved in chronic infectious disease. Particularly important diseases are hepatitis, adenovirus, polyoma virus such as BK, human immunodeficiency virus (HIV), herpes simplex virus (HSV), respiratory syncytial virus (RSV), cytomegalovirus (CMV), Epstein-Barr virus (EBV), Influenza A, B, and C, vesicular stomatitis virus (VSV), vesicular stomatitis virus (VSV), *Staphylococcus* species including Methicillin-resistant *Staphylococcus aureus* (MRSA), *Streptococcus* species including *Streptococcus pneumonia*, and post-transplant infection.

Antibodies. The term antibody is used in the broadest sense and specifically includes, for example, single monoclonal antibodies, antibody compositions with polyepitopic specificity, single chain antibodies, and antigen-binding fragments of antibodies. An antibody may include an immunoglobulin constant domain from any immunoglobulin, such as IgG1, IgG2, IgG3, or IgG4 subtypes, IgA (including IgA1 and IgA2), IgE, IgD or IgM.

In some embodiments, the therapeutic modalities used herein may be isolated. Isolated means, in the context of a biologic, the biologic has been removed from its natural milieu or has been altered from its natural state. As such, isolated does not necessarily reflect the extent to which the molecule has been removed from its natural milieu or has been altered from its natural state. However, it will be understood that a biologic that has been purified to some degree and to an extent to which it can be used for its intended therapeutic purpose is "isolated".

The antibodies used herein can be used to selectively bind their targets, for example, such as CCR2, CD34, or any of the targets used in the kits for lineage depletion.

Subject. "Subject" means a mammal, such as a human, a nonhuman primate, a dog, a cat, a sheep, a horse, a cow, a pig, a mouse, a rat, a rodent, or a goat. In an important embodiment, the subject and/or mammal is a human. in some embodiments, the subject is not receiving an immune checkpoint inhibitor.

Treatment. "Treat", "treating", "treatment", and "therapy" encompass an action that occurs while a subject is suffering from a condition which reduces the severity of the condition (or a symptom associated with the condition) or retards or slows the progression of the condition (or a symptom associated with the condition). This is therapeutic treatment.

Effective Amount. Subjects are treated with effective amounts of the solutions of the disclosure. An "effective amount" of an agent generally refers to an amount sufficient to elicit the desired biological response, i.e., treat the condition. As will be appreciated by those of ordinary skill in the art, the effective amount of an agent described herein may vary depending on such factors as the condition being treated, the mode of administration, and the age, body composition, and health of the subject.

For therapeutic treatment, an effective amount is an amount sufficient to provide a therapeutic benefit in the treatment of a condition or to reduce or eliminate one or more symptoms associated with the condition. This may encompass an amount that improves overall therapy, reduces or avoids symptoms or causes of the condition, or enhances the therapeutic efficacy of another therapeutic agent.

In general, effective amounts are administered to enhance an immune response in the subject. In connection with a specific disease or condition, "enhance an immune response" means to halt the development of, inhibit the progression of, reverse the development of, or otherwise reduce or ameliorate one or more symptoms of the disease or condition, for example, one or more symptoms of cancer or one or more symptoms of an infectious disease. In addition, effective amounts may be such amounts which slow, halt or reverse the growth of cancer cells or an infectious disease agent in the subject.

In some embodiments, an effective amount of $CCR2^+$ HSCs is any amount that increases the benefit of treatment with ACT or improves the condition of the subject being treated with ACT relative to the ACT alone, ACT and chemotherapy, or a combination of ACT and radiation therapy.

Exemplary effective amounts of mobilizing agents: Such agents are given in amounts sufficient to mobilize stem cell from bone marrow into peripheral blood. Such amounts for particular mobilizing agents have been, for example: 1 µg/kg to 20 µg/kg G-CSF per day, preferably, 5 µg/kg or 10 µg/kg G-CSF per day; 1 to 20 mg PEGylated G-CSF, preferably 6 mg or 12 mg PEGylated G-CSF; 1 to 20 µg/kg PEGylated G-CSF per day; 1 to 20 µg/kg lenogratism per day; 1 to 40 µg/m$^2$ C—X—C chemokine receptor type 4 (CXCR-4) per day; 1 to 40 µg/m$^2$ plerixafor per day.

Administration of cells is by any available means well known to those skilled in the art, In embodiments, administration of cells is typically by infusion (e.g., intravenous) or injection (e.g., subcutaneous or intratumoral) or implantation.

Timing. CCR2+ HSCs are administered close enough in time to the ACT to beneficially affect the treatment. In embodiments, practically, CCR2+ HSCs are administered 1 to 28 days, e.g., 1, 2, 3, 4, 5, 6, 7, 8, 9, 10, 11, 12, 13, 14, 15, 16, 17, 18, 19, 20, 21, 22, 23, 24, 25, 26, 27, or 28 days after completion of radiation therapy and 1 to 14 days, e.g., 1, 2, 3, 4, 5, 6, 7, 8, 9, 10, 11, 12, 13, or 14 days prior to adoptive cellular therapy. Repeated infusions of CCR2+ HSCs may be administered with subsequent cycles of ACT or with tumor-specific vaccination, typically at 1 to 6 month, e.g., 1, 2, 3, 4, 5, or 6 month, intervals.

EXAMPLES

Example 1. Bone Marrow-Derived Monocyte Populations are Highly Heterogeneous, and Distinct Subsets are Defined on the Basis of Differential Expression of Various Myeloid Markers The chemokine receptor CCR2 is expressed on monocyte precursor cells and is required for their entry into the CNS, typically as a chemotactic response to CCL2 which is expressed by KR158B glioma (Clarkson et al., 2015; Sagar et al., 2012; Flores et al., 2015). In this study, it was observed that a subset of HSCs express CCR2 (CCR2 HSC) migrate to intracranial tumor within 3 hours (data not shown). To isolate CCR2$^+$ HSCs, bone marrow was collected from non-tumor bearing mice and lineage depleted using magnetic bead separation kit (Miltenyi Biotec, Calif.). The resulting lineage negative HSCs were then further enriched with a secondary magnetic bead depletion using biotinylated anti-CCR2 antibody followed with anti-biotin bead conjugated antibody.

Figure 1B:
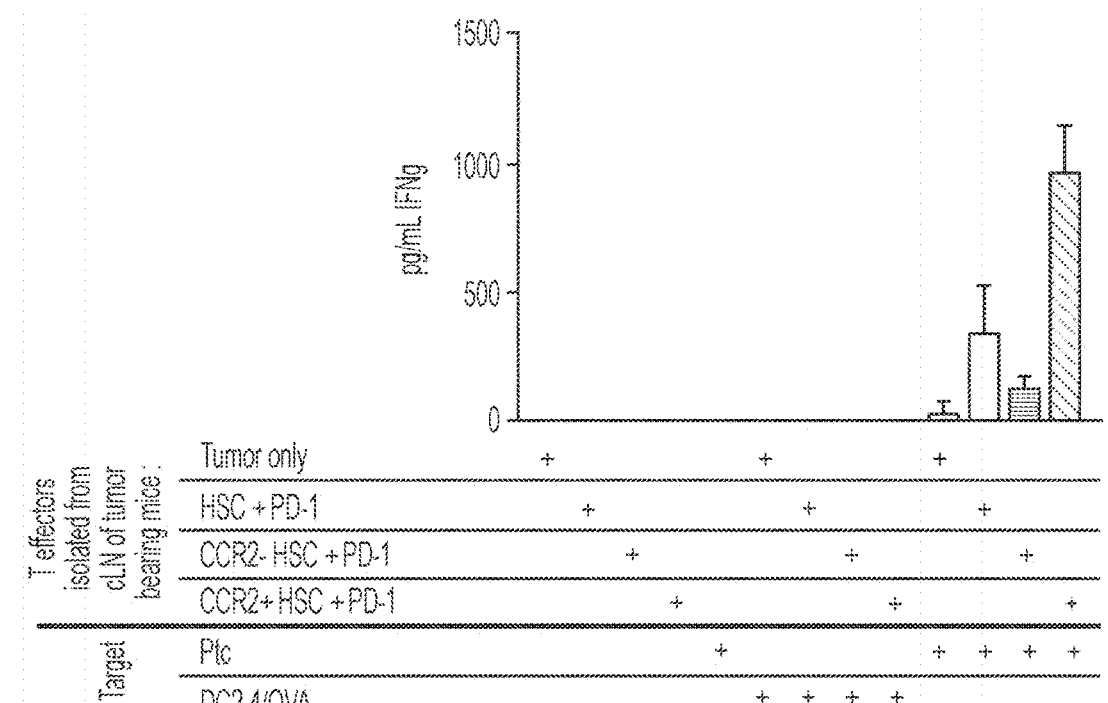
FIG. 1B shows that CCR2+HSCs can cross prime host T cells in draining lymph nodes when combined with anti-PD-1 in a medulloblastoma model.

Example 2. Determination of Whether HSC-Derived Cells Found in the Tumor Extravasate from Intracranial Tumor to Tumor Draining Lymph Nodes and Subsequently Present Tumor Antigen to Peripheral T Cells HSCs were isolated from bone marrow of non-tumor bearing mice that express DsRed reporter on beta actin promoter. DsRed$^+$ HSCs were further isolated into CCR2$^+$ HSCs or CCR2$^-$HSCs, Either DsRed$^+$HSCs, DsRed$^+$CCR2–HSCs, or DsRed$^+$CCR2$^+$ HSCs were directly injected into established intracranial KR158B tumors in vivo. After one week, tumor draining cervical lymph nodes were harvested and analyzed for presence of DsRed$^+$ HSC-derived cells. The group that received CCR2$^+$HSCs had significantly more CCR2$^+$HSC-derived cells in the lymph nodes (p=0.021 over unsorted HSCs group), demonstrating that CCR2+ HSCs give rise to cells that preferentially migrated to lymph nodes. To determine if CCR2$^+$HSC-derived cells that extravasated from the tumor to the lymph nodes have the capacity to cross-prime host peripheral T cells, the same lymph nodes were also processed for isolation of systemic T cells using a magnetic bead-based Pan T cell Depletion Kit (Miltenyi Biotec, Calif.). These T cells were then tested for anti-tumor function by co-culturing them against tumor cell targets in vitro (FIGS. 1A-1B). Astonishingly, we found that T cells isolated from tumor draining lymph nodes in the mice that received CCR2$^+$HSCs secreted IFNγ in response to tumor target while those receiving CCR2$^-$HSCs or unsorted HSCs showed inferior T cell activation based on IFNγ secretion.

Example 3. Effects of HSC Administration with ACT

Figure 2:
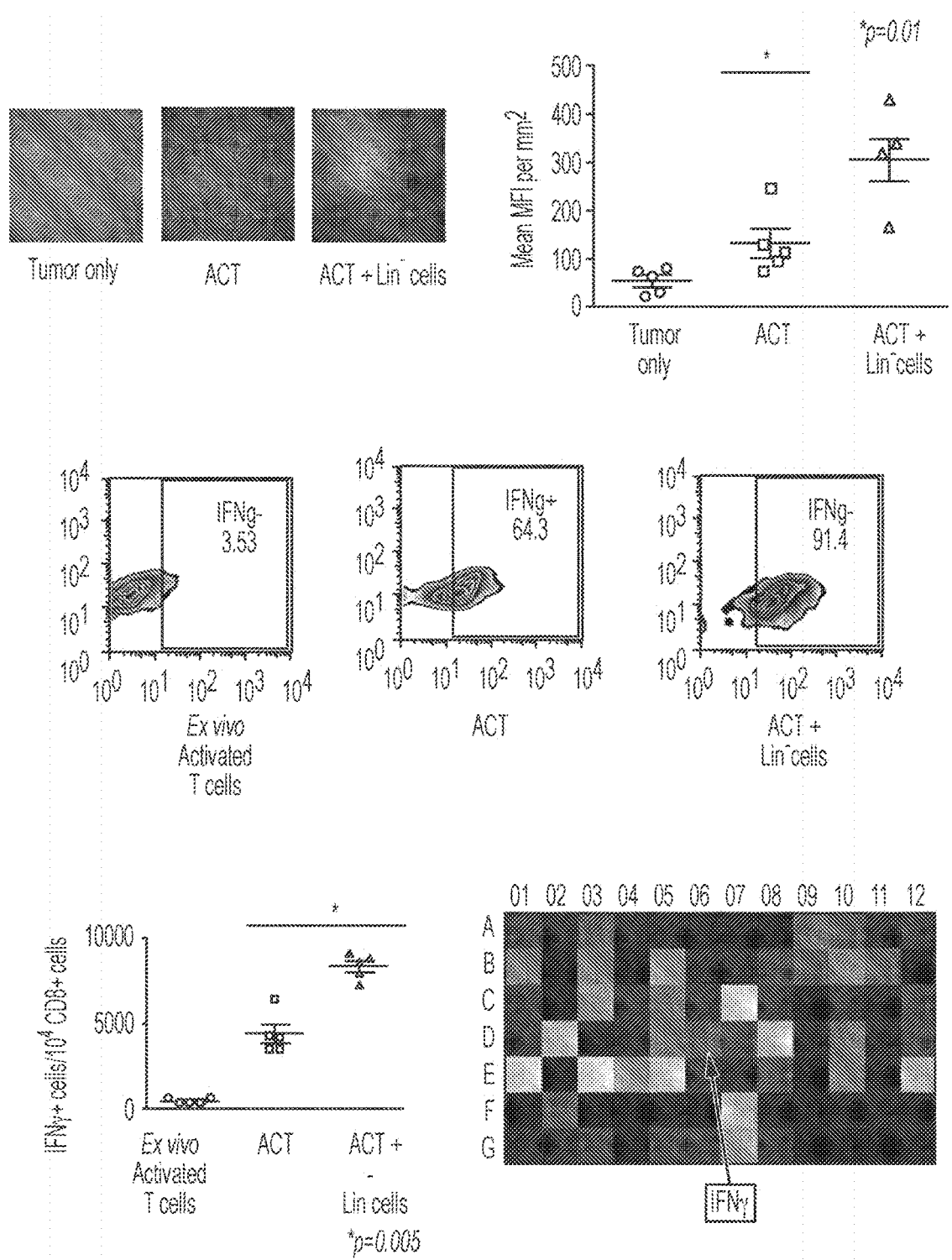
FIG. 2 shows that HSC administration with ACT significantly increases TTRNA-T cell activation and IFNγ secretion within the tumor microenvironment and in tumor draining lymph nodes relative to ACT alone. RNA from mice that received ACT+HSC versus ACT alone was analyzed using RT2 PCR Array for T- and B-cell activation.

The inventors previously demonstrated that co-transfer of HSC with adoptive cell therapy mediates intratumor migration and engraftment of tumor-specific T cells as well as suppression of early tumor growth in KR158B glioma (Flores et al., 2015). They therefore evaluated if using CCR2$^+$HSCs also enhances the efficacy of adoptive cell therapy (ACT). This ACT platform employs bone marrow-derived dendritic cells pulsed with total RNA from tumor to ex vivo expand tumor-specific T cells (TTRNA-T cells)[13]. This study demonstrates that HSC administration with ACT significantly increases TTRNA-T cell activation and IFNγ secretion within the tumor microenvironment and in tumor draining lymph nodes relative to ACT alone (FIG. 2).

Example 4. Effects of CCR2$^+$HSCs on TTRNA-T Cell Activation Within the Tumor Microenvironment To determine the impact of CCR2$^+$HSCs on TTRNA-T cell activation within the tumor microenvironment, mice with established intracranial tumors received adoptive transfer of TTRNA-T cells generated from GREAT mice, allowing for in situ detection of IFNγ secretion of these TTRNA-T cells. Mice then received intravenous administration of either CCR2$^+$HSCs or CCRTHSCs. One week later, tumors were excised and relative amounts of YFP$^+$CD3$^+$ cells within the tumor between groups was determined. Those that received CCR2$^+$HSCs expressed significantly more YFP$^+$CD3$^+$ cells than mice that received CCR2$^-$HSCs (FIG. 3A).

Example 5. Migration and Differentiation of CCR2$^+$HSCs

Figure 4:
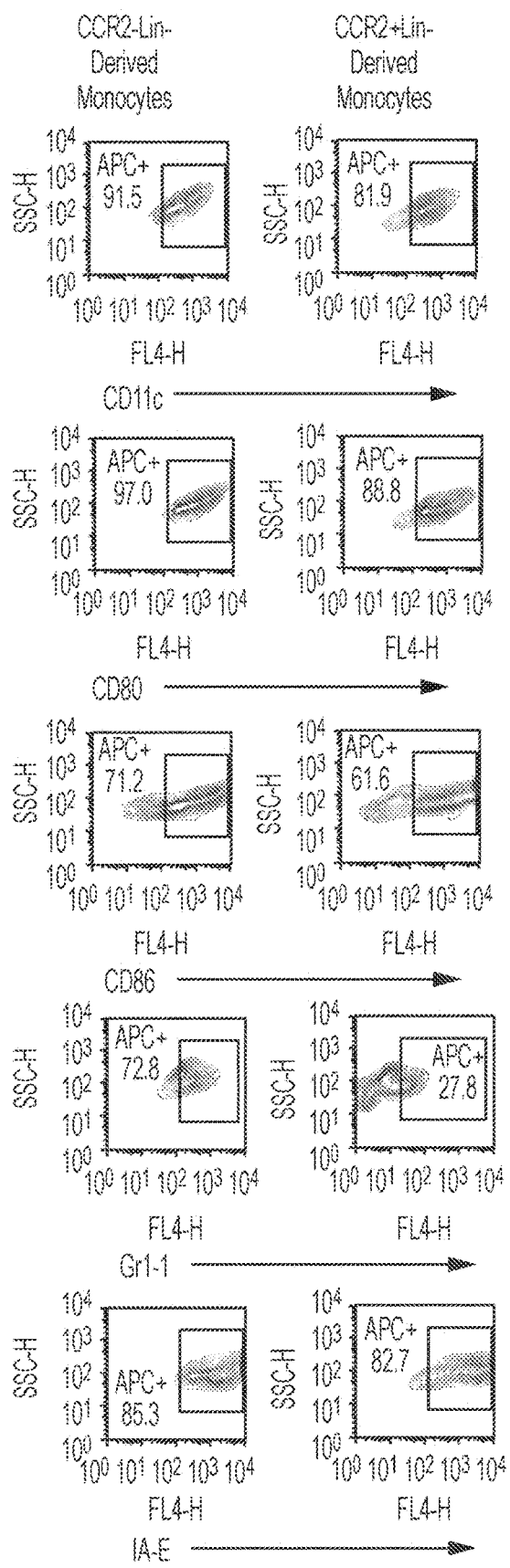
FIG. 4 shows that CCR2+HSCs differentiate into APCs in vitro. CCR2−HSCs and CCR2+HSCs were freshly isolated from murine bone marrow and cultured in vitro in previously established dendritic cell generation protocol. Resulting cells were phenotyped for markers of antigen presenting cells, CD11c, CD80, CD86, Gr1-1, MHCII. Resulting cells from either CCR2−HSCs and CCR2+HSCs were then tested for capacity to present tumor antigen. Tumor specific effector T cells were used to target either CCR2−HSC-derived cells pulsed with tumor RNA, or CCR2+HSC-derived cells pulsed with tumor RNA. IFNγ was measured as an indication of T cell recognition of cognate antigen.
Figure 4:
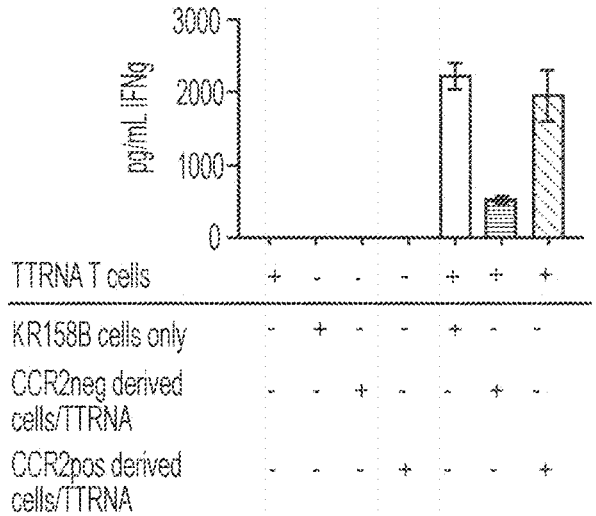

To determine if CCR2$^+$HSCs migrated to intracranial tumor, CCR2$^+$HSCs were isolated from DsRed expressing mice, while CCR2$^-$HSCs were isolated from mice that have a GFP reporter on ubiquitin promoter. Both HSC populations were injected together in equal amounts (5×10$^5$ cells) intravenously into tumor bearing mice that received host conditioning with 5 grey total body irradiation (5 Gy TBI). Twenty four hours later, tumors were excised and relative amounts of DsRed$^+$CCR2$^+$HSCs versus GFP$^+$CCR2$^-$HSCs were determined (FIG. 3B). Significantly more DsRed$^+$ CCR2$^+$HSCs accumulated within intracranial tumor within 24 hrs, interestingly, after one week within the tumor DsRed$^+$CCR2$^+$HSC-derived cells lost CCR2 expression but upregulated markers associated with antigen presenting cells, CD11c, CD80, CD86, and MHCII (FIG. 3C). To determine if CCR2$^+$HSCs have the potential to differentiate into antigen presenting cells, CCR2$^+$HSCs and CCR2$^-$HSCs were isolated from murine bone marrow and both populations were cultured in vitro using a previously established protocol for dendritic cell generation (Flores et al., 2015). Cells were then phenotyped and tested for antigen presentation capacity. Cells generated from CCR2$^+$HSCs upregulated CD11c, CD80, CD86, and MHC-II and meanwhile mounted the ability to activate antigen-specific T cells, indicating their capacity to present cognate antigen (FIG. 4).

Example 6. Presentation of Tumor Antigen by HSC-Derived

To determine if HSC-derived cells can present tumor antigen to TTRNA-T cells within in vivo tumor microenvironment, tumor bearing mice received ACT followed by intravenous administration of GFP$^+$IISCs. Three weeks post ACT, tumors were excised and GFP$^+$HSC-derived cells were isolated using FACS. These were then co-cultured in a functionality assay with TTRNA-T cells, IFNγ secretion detected by ELBA indicated TTRNA-T cell recognition of cognate antigen (FIG. 5A). Next we pursued to determine if HSC-derived cells activate CD8 or CD4 T cells, Tumor bearing mice received ACT using TTRNA-T cells generated from GREAT mice. HSCs were then isolated from MHC-I or MHC-II knockout mice and co-administered with ACT. Three weeks later, intracranial tumors were harvested and analyzed for relative expression of YFP$^+$CD3$^+$ cells (FIG. 5B). A significant decrease in T cell activation was detected in mice that received MHC-I$^{-/-}$HSCs, implying that HSC-derived cells present tumor antigen to CD8$^+$ TTRNA-T cells within the tumor microenvironment.

When HSCs are administered in these immunotherapy experiments, HSCs are freshly isolated from non-tumor bearing mice. Thus we asked how HSC-derived cells at the tumor acquire tumor antigen. To determine if irradiation plays a role in tumor antigen uptake by HSC-derived cells within the tumor, ACT and GFP$^+$HSCs were administered to late tumor bearing mice that received either 5 Gy TBI or no irradiation. Three weeks post transfer, tumors were excised and GFP$^+$ HSC-derived cells were isolated with FACS. The isolated GFP$^+$HSC-derived cells were then co-cultured with TTRNA-T cells in vitro to test detectable differences in their capacity to crossprime (FIG. 5C). Significantly more IFNγ was detected when TTRNA-T cells were co-cultured against HSC-derived cells isolated from irradiated tumor versus non-irradiated tumor.

Figure 6A:
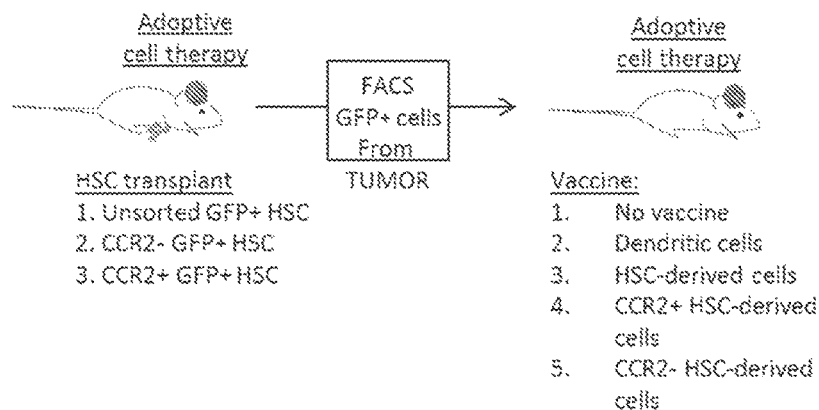
FIGS. 6A-6B show that intratumoral CCR2+HSC-derived cells cross prime tumor-specific T cells in the periphery.
Figure 6B:
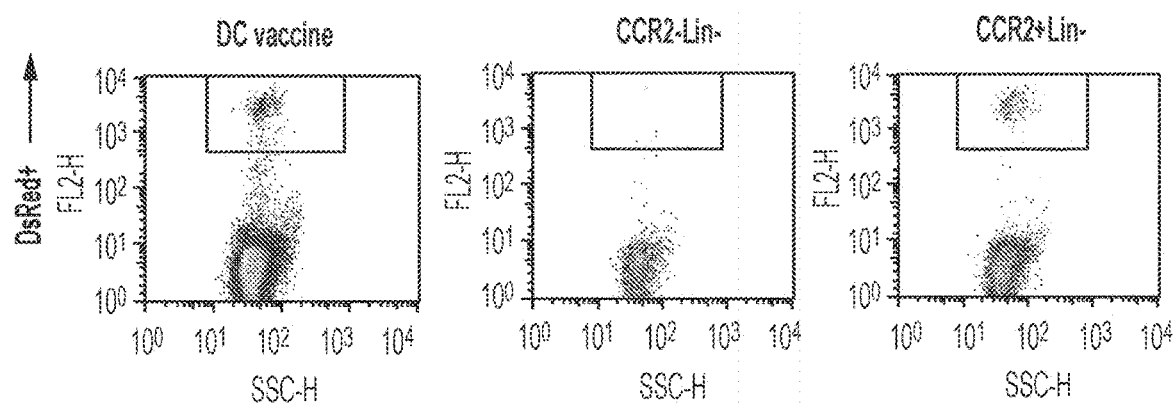

Example 7. TTRNA-T Cell Engraftment in Subjects that Received CCR2$^+$HSC-Derived Cells Our group previously published that tumor RNA-pulsed dendritic cell vaccines are responsible for the engraftment and expansion of adoptively transferred TTRNA-T cells in the periphery (Flores et al., 2015). Given this and the above described data, we conducted an experiment to determine if CCR2$^+$HPC derived cells can potentiate TTRNA-T cell engraftment and activation in vaccine draining lymph nodes as professional antigen presenting cells such as dendritic cells. Groups of mice with established tumors received ACT and either GFP$^+$HSCs, GFP$^+$CCR2$^+$HSCs, or GFP$^+$CCR2$^-$ HSCs (FIG. 6A). Three weeks after adoptive transfer, GFP$^+$ cells from all tumors were harvested and isolated using FACS. These were then used as a "vaccine" in another set of tumor bearing mice that received ACT. In these groups of mice, ACT was conducted using DsRed TTRNA-T cells then vaccinated with either no vaccine, dendritic cell vaccine, GFP$^+$HSCs derived from tumor, GFP$^+$CCR2$^+$HSC-derived cells, or GFP$^+$CCR2$^-$HSC-derived cells. One week later, vaccine draining lymph nodes were harvested and analyzed for DsRed$^+$CD3$^+$ cells to determine TTRNA-T cell engraftment (FIG. 6B). Mice that received CCR2$^+$HSC-derived cells isolated from the tumor demonstrated engraftment of DsRed$^+$CD3$^+$ TTRNA-T cells in the vaccine lymph nodes.

Example 8. Immune Potentiating Effects of CCR2$^+$HSCs on the Efficacy of ACT

Figure 7A:
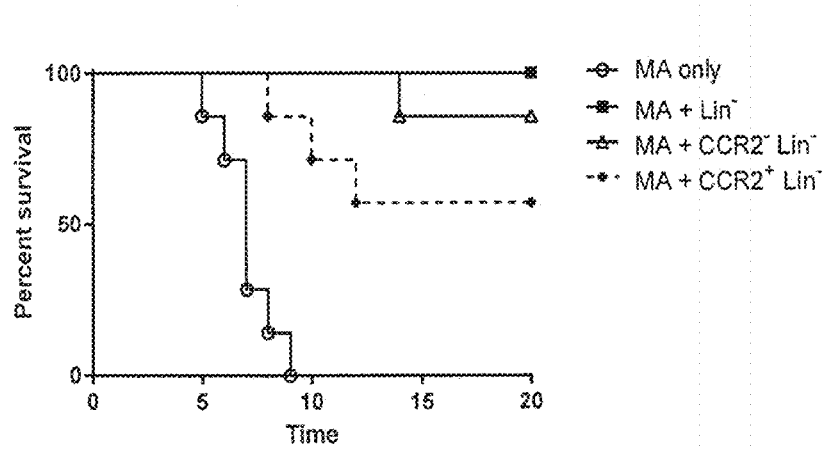
FIG. 7A shows that CCR2+HPC cells failed to rescue myeloablated host from bone marrow failure. C57BL/6 mice received myeloablative 9Gy TBI and either freshly isolated bone marrow-derived HSCs, CCR2−HSC, or CCR2+HSC (all groups received $10^5$ cells per mouse).
Figure 7B:
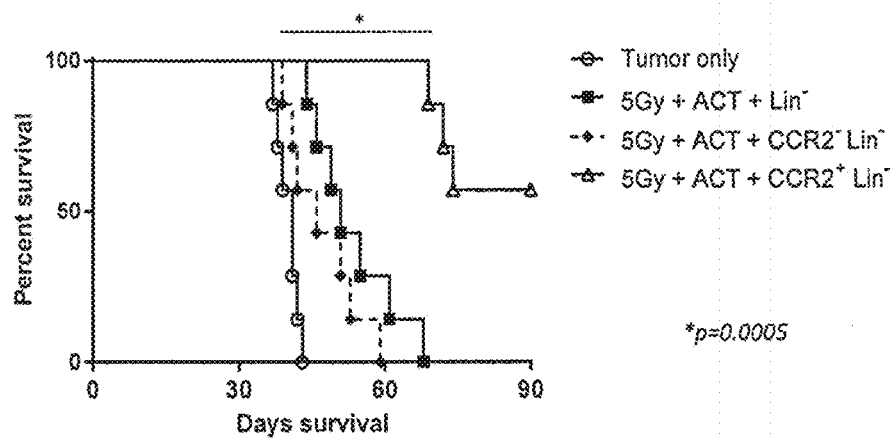
FIG. 7B shows that CCR2+HSC with adoptive cell therapy provided significant survival benefit over the use of bulk HSCs alone.

The efficacy of ACT was previously found to be dependent on myeloablative host conditioning (Flores et al., 2015). As we have demonstrated that CCR2$^+$HSC can potentiate anti-tumor immunity in both the periphery and within intracranial tumor, we sought to determine if using the CCR2$^+$HPC cells instead of our previously used HSCs would provide the efficacy we previously observed. Before using CCR2$^+$HSC cells in ACT, we first determined if CCR2$^+$HSC cells are true hematopoietic stem cells with the capacity to rescue bone marrow from myeloablative host conditioning. Naïve mice received myeloablation (MA) using 9 Gy TBI. Groups received either MA only, MA$^+$HSC cells, MA$^+$CCR2$^+$HSC cells, or MA$^+$CCR2$^-$HSC cells. CCR2$^+$HPC cells failed to rescue myeloablated host from bone marrow failure (FIG. 7A). Therefore, to determine if the immune potentiating effects of CCR2$^+$HSCs impact the efficacy of ACT, non-myeloablative (NMA) 5 Gy TBI host conditioning was used. Groups of intracranial KR158B tumor bearing mice received non-myeloablative 5 Gy TBI followed by ACT and co-transfer of HSCs, CCR2$^+$HSC, or CCR2$^-$HSC (FIG. 7B). The use of CCR2$^+$HSC with adoptive cell therapy provided significant survival benefit over the use of bulk HSCs alone (p=0.0005). We demonstrate that this population of CCR2$^+$lin-bone marrow derived cells mediates increased T cell activation in combination with adoptive T cell strategies.

Example 9. CCR+ Hematopoietic Stem Cells Mediate T Cell Activation in Adoptive Cell Therapy Co-transfer of CCR2$^+$ HSCs with adoptive cell therapy led to markedly increased survival benefit in multiple brain tumor models. We found that intravenously administered CCR2+ HSCs migrate preferentially to the CNS tumor microenvironment, differentiate into CD11c+ antigen presenting cells (APCs) at the tumor site, and reprogram gene expression within the immunosuppressive tumor microenvironment. Additionally, the APCs derived from CCR2+ HSCs uniquely cross-present tumor-derived antigens to CD8+ and CD4+ tumor reactive lymphocytes leading to prolonged intratumoral T cell activation and enhanced tumor rejection.

Figure 8:
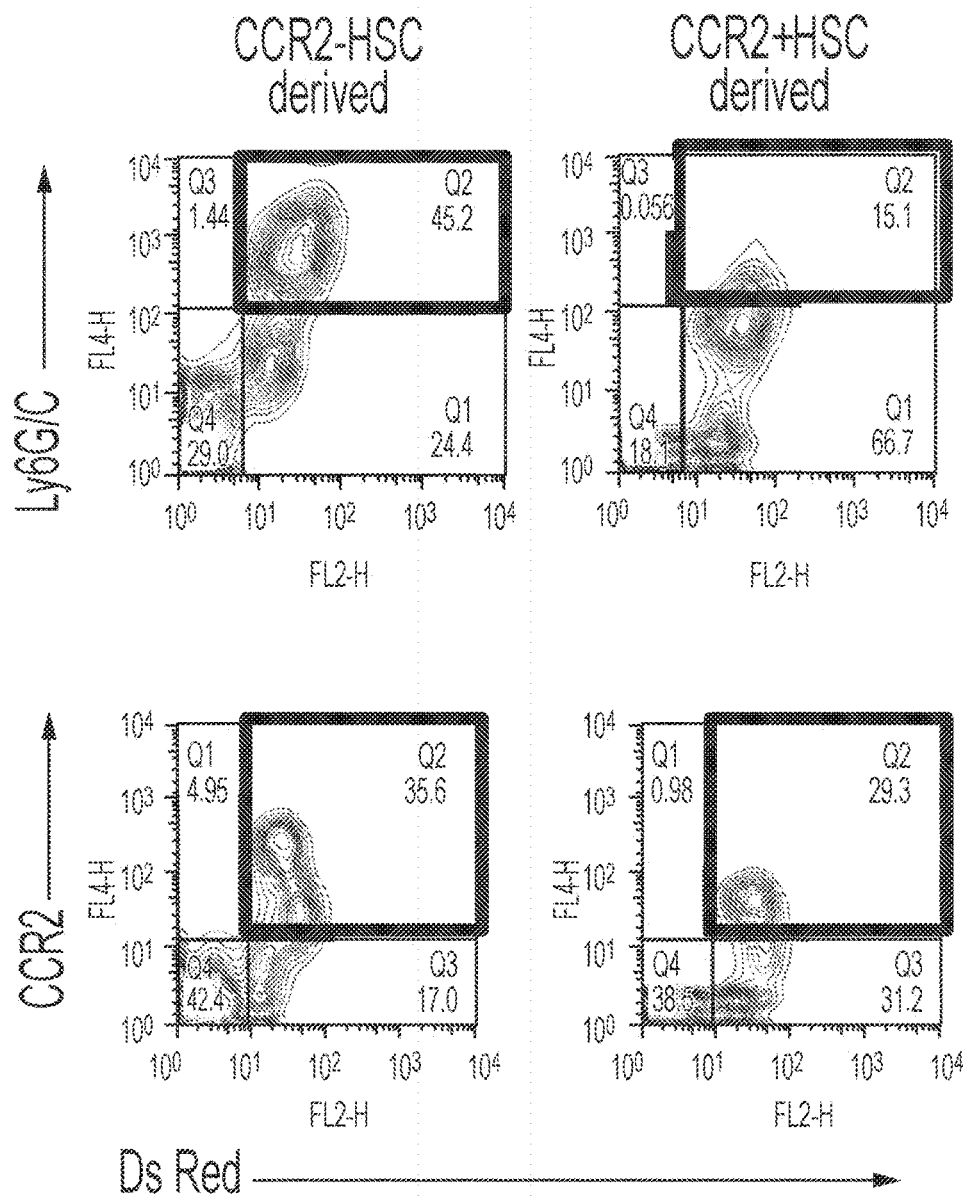
FIG. 8 shows Tumor bearing mice received adoptive cell therapy with either CCR2+HSCs or CCR2−HSCs. One week post-ACT, HSC-derived cells were isolated from the tumors and phenotyped using flowcytometry.
Figure 9:
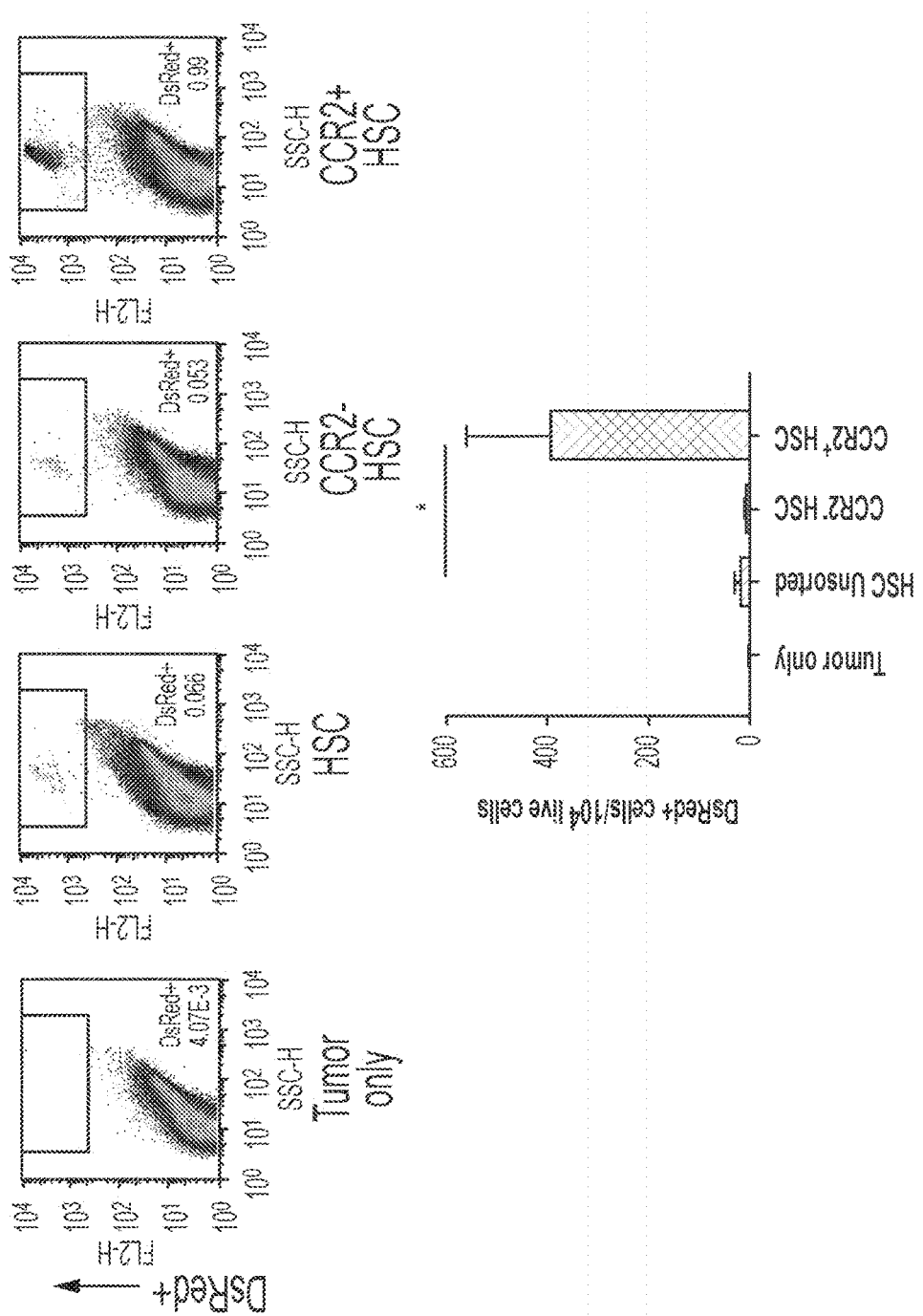
FIG. 9 shows tumor bearing mice received injection of DsRed+HSCs, CCR2−HSC, or CCR2+HSC directly into the tumor. One week later, tumor draining cervical lymph nodes were excised and relative amounts of DsRed+ cells were quantified by flow cytometry to determine if HSC-derived cells extravasate from the tumor into secondary lymphoid organs. Groups that received CCR2+HSCs versus CCR2− HSCs had significantly higher amount of DsRed+ cells in the draining lymph nodes (p=0.0480; unpaired t test).

We have demonstrated that cells derived from CCR2+ HSC may differentiate into antigen presenting cells within the tumor. We postulated if these antigen presenting cells present in the intracranial tumor have the capacity to present tumor antigen to T cells in draining lymph nodes. First, to determine if HSC-derived cells found in the tumor extravasate from intracranial tumor to draining lymph nodes, DsRed+HSCs, DsRed+CCR2−HSCs, or DsRed+CCR2+HSCs were directly injected into established intracranial KR158B tumors in vivo. After one week, draining cervical lymph nodes were harvested and analyzed for presence of DsRed+ cells. The group that received CCR2+ HSCs had significantly more DsRed+ cells in the lymph nodes (p=0.021 over unsorted HSC group, p=0.0480 vs CCR2− HSCs)((FIG. 8). The T cells from these draining lymph nodes were tested for anti-tumor function by co-culturing them against target tumor cells in vitro (FIGS. 1A/1B). Mice that received intracranial injection of CCR2+ HSCs demonstrated increased IFN-γ secretion by peripheral T cells in response to tumor antigens, suggesting that these T cells were primed against tumor antigen, presumably by the cells derived from the CCR2+HSCs that differentiated into antigen presenting cells in the tumor and extravasated into the draining lymph node.

Figure 10A:
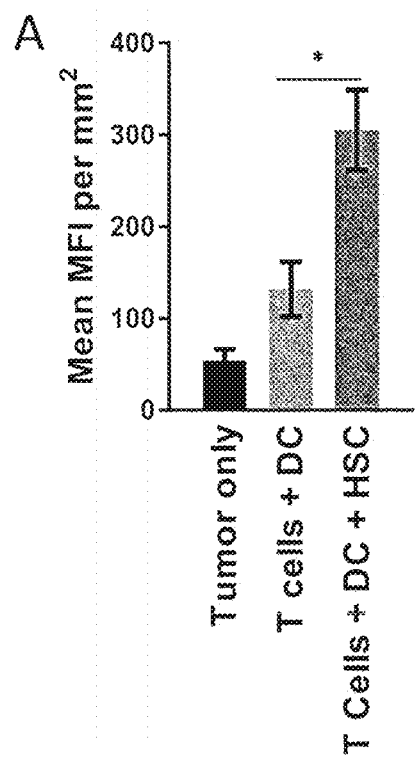
FIG. 10A shows C57BL/6 mice received ACT using tumor-specific T cells generated from GREAT mice which express YFP on the IFNγ promoter. In groups that received HSC co-transfer with ACT, greater YFP expression was detected within tumor. Mean fluorescence intensity was measured across whole brain slices containing tumor.
Figure 10B:
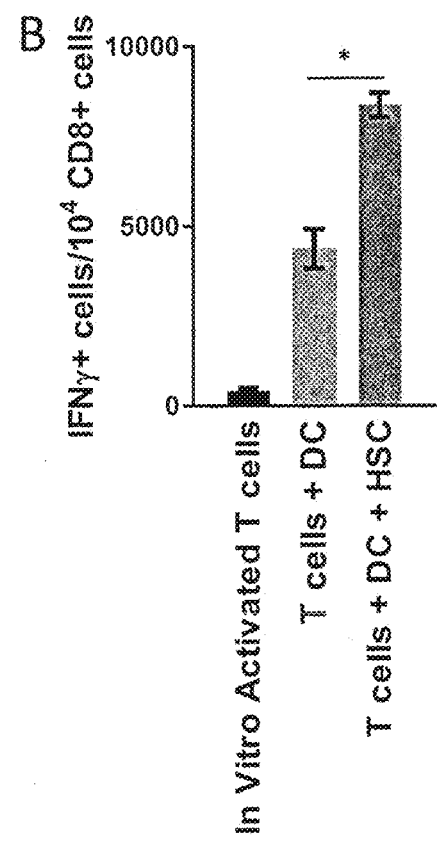
FIG. 10B shows that tumor draining lymph nodes were also isolated and analyzed for YFP expression of CD8+ T cells using flow cytometry.

In addition to checkpoint blockade, adoptive cell therapy is demonstrably impactful against solid tumors (Rosenberg S A. Raising the bar: the curative potential of human cancer immunotherapy. Science translational medicine. 2012; 4(127):127ps8; Rosenberg S A. Cell transfer immunotherapy for metastatic solid cancer—what clinicians need to know. Nat Rev Clin Oncol. 2011; 8(10):577-85.). Studies in murine and human systems have demonstrated that efficacy of adoptive cell therapy is enhanced after lymphodepletive host conditioning followed with HSC transfer (Wrzesinski C, Paulos C M, Gattinoni L, Palmer D C, Kaiser A, Yu Z, Rosenberg S A, and Restifo N P. Hematopoietic stem cells promote the expansion and function of adoptively transferred antitumor CD8 T cells. J Clin Invest. 2007; 117(2): 492-501). We previously demonstrated that co-transfer of lin-HSCs with adoptive cell therapy mediates migration and engraftment of tumor-specific T cells as well as suppression of tumor growth in KR158B glioma (Flores C, Pham C, Snyder D, Yang S, Sanchez-Perez L, Sayour E, Cui X, Kemeny H, Friedman H, Bigner D D, et al. Novel role of hematopoietic stem cells in immunologic rejection of malignant gliomas. Oncoimmunology. 2015; 4(3):e994374). We evaluated if the CCR2+HSCs were the active component of the bulk HSC population responsible for the enhancement of adoptive cell therapy (ACT). ACT employs bone marrow-derived dendritic cells (DCs) pulsed with total tumor RNA to ex vivo expand tumor-specific T cells (Flores, C. et al. Novel role of hematopoietic stem cells in immunologic rejection of malignant gliomas. Oncoimmunology 4, e994374, doi:10.4161/2162402X.2014.994374 (2015)). We found that HSC administration with ACT significantly increases tumor-specific T cell activation and IFN-γ secretion within the tumor microenvironment and in draining lymph nodes relative to ACT alone (p=0.011) (FIGS. 10A, 10B, and FIG. 2).

Figure 11:
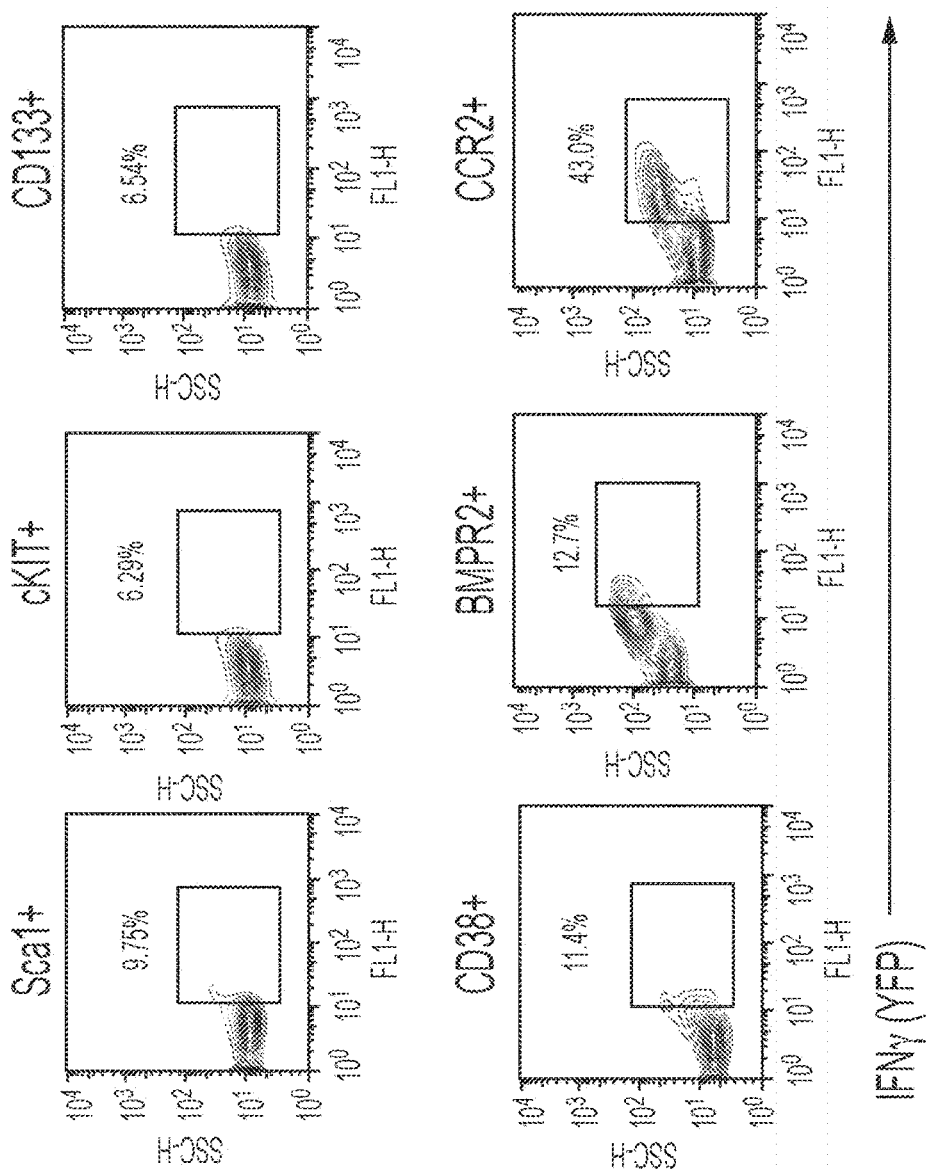
FIG. 11 shows tumor bearing mice received ACT using TTRNA T cells generated from GREAT mice to longitudinally track T cell activation. This was followed with co-transfer of bone marrow derived lineage negative HSCs as defined by Sca1, cKit, CD133, CD38, BMPR2, or CCR2. One week post cell transfer, tumors were excised and levels of YFP were measured to determine which subpopulation leads to increased T cell activation.

To determine the impact of CCR2+HSCs on T cell activation within the tumor microenvironment, mice with established tumors received adoptive transfer of tumor-specific T cells generated from GREAT mice, allowing for in situ detection of IFN-γ secretion of these T cells. Mice received intravenous CCR2+HSCs or CCR2−HSCs. Tumors were excised and relative expression of YFP+CD3+ cells within the tumor was determined. Those that received CCR2+HSCs versus CCR2−HSCs expressed significantly more YFP+CD3+ cells (19.2% vs 6.3%, p=0.0002) (FIG. 3a). Other progenitor subsets derived from lin-HSCs (Sca-1+, c-Kit+, CD133+, CD38+, BMPR2+) were evaluated for their capacity to activate tumor-reactive lymphocytes and CCR2+HSCs were markedly superior in enhancing anti-tumor immunity (FIG. 11).

To determine if these HSC subsets migrate to intracranial tumor, DsRed+CCR2+HSCs and GFP+CCR2−HSCs were intravenously injected in equal amounts (5×105 cells) into lymphodepleted tumor-bearing mice. Twenty-four hours later, relative amounts of DsRed+CCR2+HSCs versus GFP+CCR2−HSCs was measured in the tumor. Significantly more DsRed+CCR2+HSCs accumulated within intracranial tumor at 24 hrs (p=0.0010). As previously demonstrated, after one week, DsRed+CCR2+HSC-derived cells lost CCR2 expression but upregulated markers associated with APCs, CD11c, CD80, CD86, and MHC-II (FIG. 3C and FIG. 8). CCR2+ HSCs and CCR2−HSCs were isolated and cultured in vitro under dendritic cell generation conditions(12) to examine differentiation into antigen presenting cells. Antigen presenting cells from CCR2+HSCs had a distinct dendritic cell phenotype while cells that arose from CCR2−HSCs upregulated expression of monocyte suppressor cell marker Ly6G (Gr1-1)(FIG. 4). In addition, cells derived from CCR2+ HSCs were markedly superior in presenting tumor antigens in vitro over cells that arose from CCR2−HSCs (FIG. 4).

Figure 12:
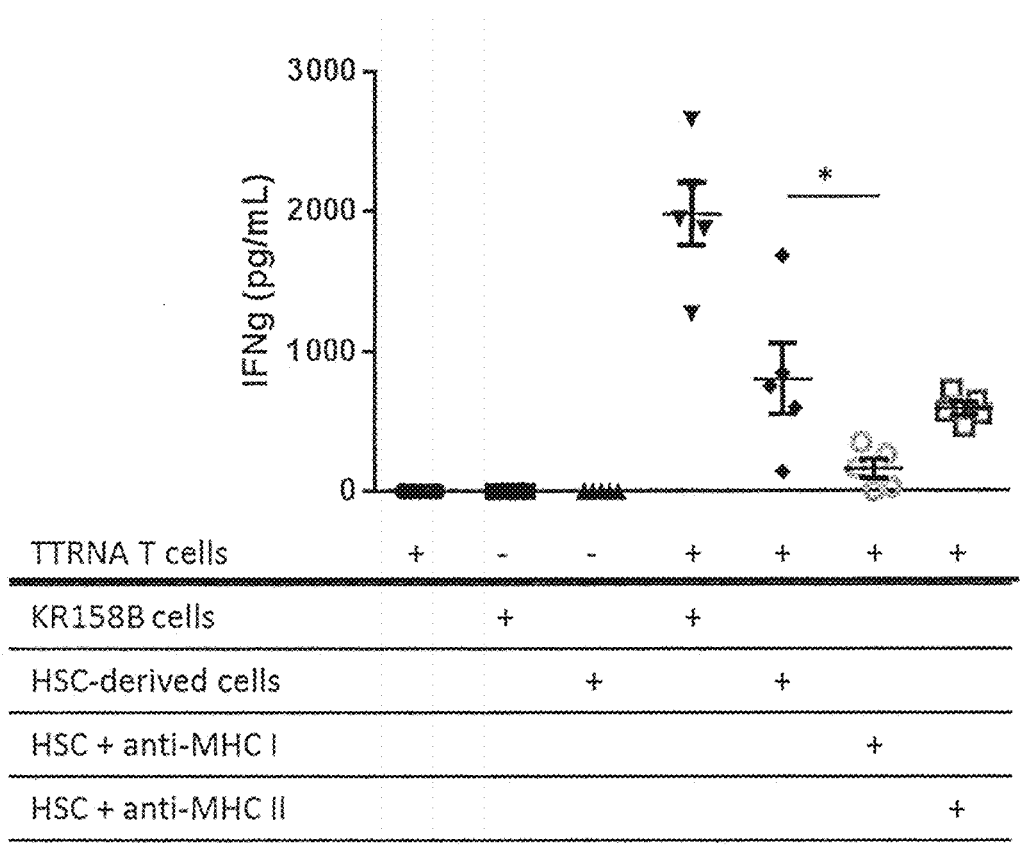
FIG. 12 shows either MHC I or MHC II was blocked by addition of blocking antibodies in the in vitro co-culture functionality assay. Mean IFNγ for HSC-derived group was 802.4 pg/mL versus 161.6 in HSC-derived+anti-MHC I group, p=0.0390 unpaired t test. No significant decrease in IFNγ was detected in the group blocking MHC II.

To determine if HSC-derived cells capture and present tumor antigens within the tumor microenvironment, mice received HSCs from syngeneic GFP transgenic mice. Three weeks post adoptive cell therapy, GFP+HSC-derived cells were isolated from the tumor using FACS. These were then co-cultured with anti-tumor TTRNA-T cells and demonstrated specific presentation of tumor-derived antigens (FIG. 5A). To determine if HSC-derived cells have the capacity to present antigen to CD4 or CD8 tumor-specific T cells, HSC-derived cells were again isolated with FACS and MHC-I or MHC-II was blocked using blocking antibody before culturing against effector tumor-specific T cells (FIG. 12). A significant decrease in IFNγ secretion was observed after blocking MHC-I. To confirm that HSC-derived cells mount the capacity to present antigen to T cells, HSCs were then isolated from MHC-I or MHC-H knockout mice and co-administered with ACT. Three weeks later, tumors were harvested and analyzed for expression of YFP+CD3+ cells (FIG. 5B). A significant decrease in T cell activation was detected in mice that received MHC-I−/−HSCs versus wild-type HSCs (p=0.0002), demonstrating that cross-presentation of tumor antigen in the class I pathway by HSC-derived cells is critical for in vivo T cell activation within the CNS tumor microenvironment.

To further demonstrate the unique cross-priming capacity of antigen presenting cells derived from CCR2+HSCs, we isolated antigen presenting cells directly from the tumors of mice receiving adoptive cell therapy and used them as a cellular vaccine in recipient mice receiving DsRed+ tumor-specific T cells. Tumor-bearing mice received adoptive cell therapy and either GFP+HSCs, GFP+CCR2+HSCs, or GFP+CCR2−HSCs (FIG. 6A). Three weeks post-adoptive cell therapy, GFP+ cells from all tumors were harvested and isolated using FACS. These were then used as a "vaccine" in another set of tumor-bearing mice that received adoptive cell therapy. This cohort received either no vaccine, DC vaccine (TTRNA DC), or antigen presenting cells isolated from the tumor microenvironment derived from GFP+ HSCs, GFP+CCR2+HSC-derived cells, or GFP+CCR2−HSC-derived cells. Vaccine-site draining lymph nodes were harvested and analyzed for expansion of DsRed+CD3+ T cells and demonstrated that CCR2+HSCs led to the expansion of tumor-reactive T cells in vivo (FIG. 6B). Collectively, these experiments demonstrate that CCR2+HSCs uniquely give rise to APCs that capture tumor antigen in vivo and cross-present tumor antigens to CD8+ T cells in vitro and in vivo.

Figure 13A:
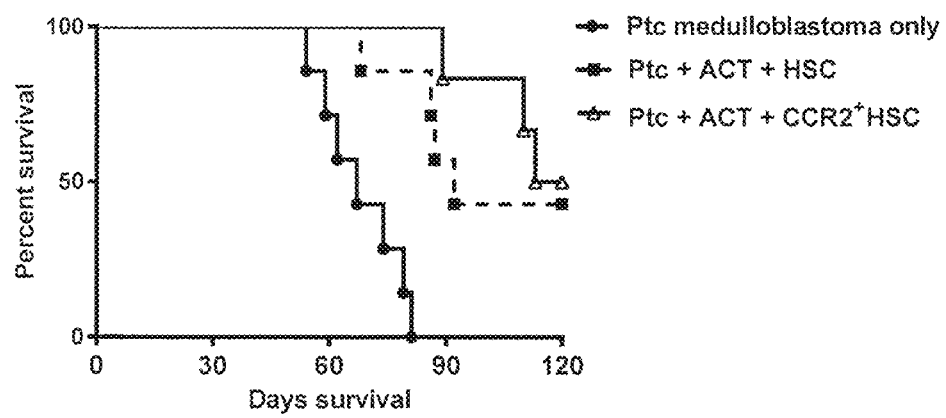
FIG. 13A shows C57BL/6 mice received cerebellar Ptc medulloblastoma tumor followed by lymphodepletive host conditioning and adoptive cell therapy with either bulk HSCs or CCR2+HSCs.
Figure 13B:
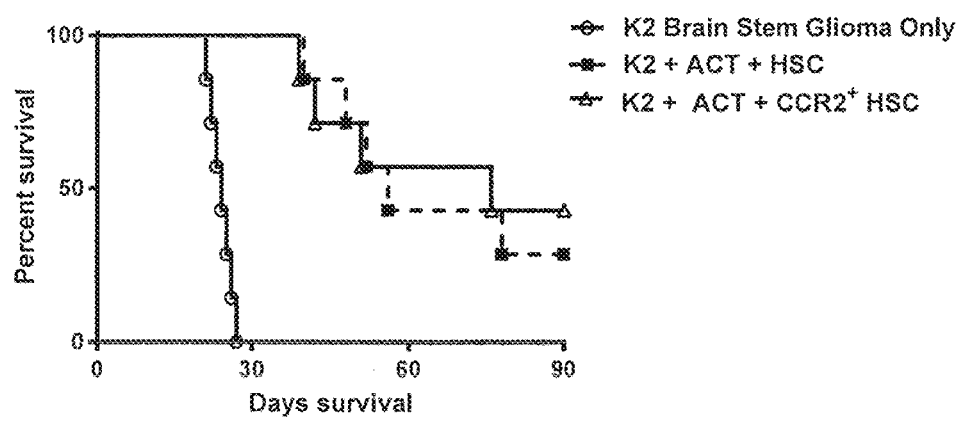
FIG. 13B shows C57BL/6 mice received transplant of K2 brain stem glioma into their brain stems followed by lymphodepletive host conditioning and adoptive cell therapy with either bulk HSCs or CCR2+HSCs.
Figure 14:
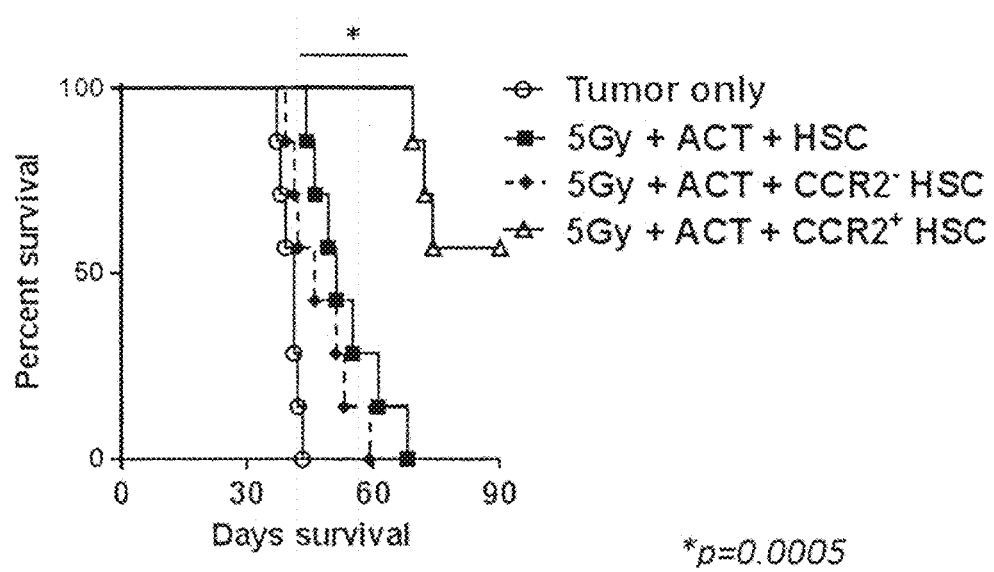
FIG. 14 shows KR158B intracranial tumor bearing mice received lymphodepletive host conditioning with 5Gy TBI prior to adoptive cell therapy. Cohorts received either bulk HSCs, CCR2−HSCs, or CCR2+HSCs. Mice that received CCR2+HSCs had increased median survival (undefined) over mice that received bulk HSCs (51 days)(p=0.0005).

To determine if lin-CCR2+HSCs are true hematopoietic stem cells that provide rescue from bone marrow failure, CCR2+HSCs or CCR2−HSCs were intravenously administered into myeloablated hosts (9 Gy TBI). Lin-CCR2+HSCs were less efficient in rescuing hosts from lethal irradiation, suggesting a progenitor population (FIG. 7A). To determine if CCR2+HSCs are responsible for the enhanced efficacy of stem cell transfer in adoptive cellular therapy targeting brain tumors, purified CCR2+HSCs versus CCR2−HSCs were transferred in conjunction with adoptive cell therapy in mice receiving non-myeloablative conditioning (5 Gy TBI). CCR2+HSCs were markedly superior in enhancing the efficacy of adoptive cellular therapy against glioma ($p=0.0005$) (FIG. 14) and medulloblastoma, and provided equal survival benefit against brain stem glioma (FIG. 13). These findings are the first to identify a bone marrow-derived progenitor cell population that has the capacity to alter the tumor microenvironment and enhance response to immune checkpoint blockade and adoptive cellular therapy. These findings alter our understanding of the role of stem cell transplantation in the treatment of solid malignancies and hold relevance for addressing resistance to cancer immunotherapy.

Materials and Methods:

Mice. Female six- to eight-week-old C57BL/6 mice (Jackson Laboratories, stock #000664), transgenic DsRed mice (Jackson Laboratories, stock #006051), and transgenic GREAT mice (Jackson Laboratories, stock #017580) were used for experiments. The investigators adhered to the "Guide for the Care and Use of Laboratory Animals" as proposed by the committee on care of Laboratory Animal Resources Commission on Life Sciences, National Research Council. The facilities at the University of Florida Animal Care Services are fully accredited by the American Association for Accreditation of Laboratory Animal Care, and all studies were approved by the University of Florida Institutional Animal Care and Use Committee.

RNA isolation. Total tumor RNA isolation from tumor cell lines was performed with RNeasy mini kit (Qiagen, cat #74104) as per the manufacturer's protocol.

Tumor-specific T cells. Tumor-reactive TTRNA-T cells were generated as previously described(Flores et al., 2015). Briefly, bone marrow-derived dendritic cells were harvested from C57BL/6 mice and cultured in GM-CSF (18 ng/mL, R&D, cat #415-ML/CF) and IL-4 (18 ng/mL, R&D, cat #404-ML/CF) for 9 days. Dendritic cells were then electroporated with 25 ug total RNA isolated from tumor tissue. Naïve mice were primed with $2.5 \times 10^5$ total tumor RNA-pulsed dendritic cells. After one week, splenocytes were then harvested and co-cultured ex vivo using total tumor RNA-pulsed dendritic cells and IL-2 (50 U/mL, R&D, cat #402-ML/CF) for 5 days. $10^7$ T cells were intravenously administered for adoptive cell therapy.

Tumor models. Tumor-bearing experiments were performed in syngeneic sex-matched C57BL/6 mice. The KR158B(9) glioma line (provided by Dr. Karlyne M. Reilly, National Cancer Institute) was verified histologically as high-grade glioma and gene expression analysis by RNASeq demonstrating appropriate haplotype background and expression of astrocytoma-associated genes. $10^4$ KR158B cells were implanted into the caudate nucleus by injecting 2 mm lateral to the midline and 3 mm deep (Reilly K M, Loisel D A, Bronson R T, McLaughlin M E, and Jacks T. Nf1;Trp53 mutant mice develop glioblastoma with evidence of strain-specific effects. Nat Genet. 2000; 26(1):109-13.; Flores et al., 2015). Ptc tumor cells were derived directly from Ptc+/− transgenic mice developing spontaneous tumors. Tumors were serially passaged in vivo in wild-type C57BL/6 mice and verified by gene expression analysis for consistency with Ptc+/− murine medulloblastoma (Pham C D, Flores C, Yang C, Pinheiro E M, Yearley J H, Sayour E J, Pei Y, Moore C, McLendon R E, Huang J, et al. Differential Immune Microenvironments and Response to Immune Checkpoint Blockade among Molecular Subtypes of Murine Medulloblastoma. Clin Cancer Res. 2016; 22(3): 582-95). For experiments using Ptc medulloblastoma, $1.25 \times 10^5$ Ptc cells were implanted into the cerebellum 1 mm lateral to midline and 3 mm deep (Pham et al., 2016; Goodrich L V, Milenkovic L, Higgins K M, and Scott M P. Altered neural cell fates and medulloblastoma in mouse patched mutants. Science. 1997; 277(5329):1109-13). For experiments using brain stem glioma cells (provided by Dr. Oren Becher), $10^5$ cells were implanted stereotactically into the brain stem of mice 1 mm infratentorial on midline and 3.5 mm in depth.

Adoptive Cell Therapy. Treatment of tumor-bearing mice began with 5 Gy lymphodepletion or 9 Gy myeloablation on day 5 post-tumor injection with X-ray irradiation (X-RAD 320, Precision X-ray). On day 6 post-intracranial tumor injection, mice received a single intravenous injection with $10^7$ autologous ex-vivo expanded TTRNA T cells with either $5 \times 10^4$ lineage-depleted (lin-) hematopoietic stem and progenitor cells (HSCs) (MiltenyiBiotec, cat #130-090-858), CCR2+ lin-HSCs, or CCR2 −lin-HSCs. CCR2 positive selection was conducted using biotinylated anti-mouse CCR2 antibody followed by anti-biotin microbead separation. Beginning day 7 post-tumor injection, $2.5 \times 10^5$ tumor RNA-pulsed dendritic cell vaccines were injected intradermally posterior to the ear pinna weekly for three total vaccine doses.

Mouse lymph node. Lymph nodes were dissected bilaterally from the cervical region of treated mice. Lymph nodes were mechanically dissociated and chemically digested with 2% collagenase (Fisher Scientific, cat #10103578001) for 30 minutes.

Brain Tumor Digestion. Tumor resection extended to gross borders of tumor mass near the site of injection. Tumors were dissociated mechanically with a sterilized razor blade and chemically with papain (Worthington, cat #NC9809987) for 30 minutes then filtered with a 70 μm cell strainer prior to antibody incubation.

Flow cytometry and antibodies. Flow cytometry was performed on FACS Canto-II and FACS sorting was performed on the FACSAria II. Cells were prepared ex-vivo as described above and suspended in 2% FBS (Seradigm, cat #97068-091) in PBS (Gibco, cat #10010-049). Antibodies below were applied per manufacturer's recommendation with isotype controls. Anti-CD3 (BD, cat #553066), anti-CD11c (Affymetrix, cat #17-0114-82), anti-CD80 (Affymetrix, cat #17-0801-82), anti-CD86 (Affymetrix, cat #17-0862-82), anti-Ly-60/6C (BD Biosciences, cat #553129), and anti-MHC II IA-E (Affymetrix, cat #17-5321-82), Anti-mouse MHC Class II (I-A/I-E) blocking antibody (Affymetrix, cat #16-5321-85) and anti-mouse MHC Class I (H-2K.) blocking antibody (Affymetrix, cat #16-5957-85).

T cell function assay. In-vitro experiments utilized IFN-γ release as a measure of T cell activity in which effector cells and targets are co-cultured in a 10:1 ratio in 96-well U-bottom plates in triplicate. IFN-γ Platinum ELISAs (Affymetrix, cat #BMS606) were performed on harvested and frozen acellular media from the supernatants of the 96-well co-culture plates after 1 day of co-culture.

Anti-PD-1 blocking antibody. Administration of anti-PD-1 blocking antibody (Merck, mDX-400) began on the day of T cell administration and continued every 5 days for a total of four doses of 10 mg/kg(8).

PCR Array. PCR analysis was performed on tumors excised from treated mice. Tumors were dissociated and RNA isolated as described above and analysed with the RT2 Profiler Array Cancer Inflammation and Immunity Crosstalk (Qiagen, cat #PAMM-181ZD-12) or T cell and B cell Activation (Qiagen, cat #PAMM-053ZD-2) as per manufacturer's protocol.

Statistical analysis. Statistics were reviewed by Paul Kubilis, M S, the biostatistician in the UF Department of Neurosurgery. All experiments were analysed in Prism 7 and tests were applied as described in the figure legends. The median survival for tumor bearing animals is 25-42 days for mice in the experiments described in this protocol. Because we are interested in significant differences in survival and/or tumor size between our experimental groups (4.5 fold increase or greater) as few as 7 animals per group is sufficient to detect statistically significant results with the given therapies. Of primary interest are pairwise comparisons of survival with the control arm. To account for the multiplicity of tests or comparisons, a significance level of 0.0125 will be used (i.e. Bonferroni correction of 0.05/4). With 10 animals in each arm each pairwise comparison will have 80% power to detect a 4.5-fold increase in the median survival in the experimental arm relative to the median of 25 days expected in the control arm. Because of variance in therapeutic effects demonstrated in our experimental mice, using 10 animals in certain experiments (versus 7) is required to conduct sufficient statistical analysis. All survival outcome experiments outlined in this proposal use 7-10 animal groups because of this statistical validation. The log-rank test was utilized to compare Kaplan-Meier survival curves. An unpaired, Mann-Whitney rank sum test was applied for two-group comparisons for in-vivo experiments. An unpaired, Student's t-test was applied for two-group comparisons for in-vitro experiments. The data have normal distribution and variance was similar between groups statistically compared. Significance is determined as $p<0.05$. For animal studies where tissue was analysed for biological endpoints, n=5 mice per group and no statistical methods were used to determine sample size. The authors pre-established that no animals or samples were to be excluded from analysis. For randomization of animal experiments, mice were housed at 5 mice per cage. After tumor implantation, mice were immediately randomized to cages.

REFERENCES

Rosenberg S A. Raising the bar: the curative potential of human cancer immunotherapy. Science translational medicine, 2012; 4(127):127ps8.

Rosenberg S A. Cell transfer immunotherapy for metastatic solid cancer—what clinicians need to know. Nat Rev Clin Oncol. 2011; 8(10):577-85.

Clarkson, B. D. et al. CCR2-dependent dendritic cell accumulation in the central nervous system during early effector experimental autoimmune encephalomyelitis is essential for effector T cell restimulation in situ and disease progression. J Immunol 194, 531-541, doi:10.4049/jimmunol.1401320 (2015).

Sagar, D. et al. Dendritic cell CNS recruitment correlates with disease severity in EAE via CCL2 chemotaxis at the blood-brain barrier through paracellular transmigration and ERK activation. J Neuroinflammation 9, 245, doi:10.1186/1742-2094-9-245 (2012).

Flores, C. et al. Novel role of hematopoietic stem cells in immunologic rejection of malignant gliomas. Oncoimmunology 4, e994374, doi:10.4161/2162402X.2014.994374 (2015).

Reilly K M, Loisel D A, Bronson R T, McLaughlin M E, and Jacks T. Nf1;Trp53 mutant mice develop glioblastoma with evidence of strain-specific effects. Nat Genet. 2000; 26(1):109-13.

Pham C D, Flores C, Yang C, Pinheiro E M, Yearley J H, Sayour E J, Pei Y, Moore C, McLendon R E, Huang J, et al. Differential Immune Microenvironments and Response to Immune Checkpoint Blockade among Molecular Subtypes of Murine Medulloblastoma. Clin Cancer Res. 2016; 22(3): 582-95.

Goodrich L V, Milenkovic L, Higgins K M, and Scott M P. Altered neural cell fates and medulloblastoma in mouse patched mutants. Science. 1997; 277(5329):1109-13.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

Equivalents

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. it is, therefore, to be understood that the foregoing embodiments are presented by way of example only and that, within the scope of the appended claims and equivalents thereto, inventive embodiments may be practiced otherwise than as specifically described and claimed. inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

That which is claimed is:

1. A method of treating a disease selected from cancer or an infectious disease in a subject, comprising administering to the subject having the disease adoptive cell therapy (ACT) and administering to the subject a preparation containing hematopoietic stem cells, in amounts effective to treat the disease, wherein the hematopoietic stem cells (HSCs) are enriched for CCR2 positive (CCR2+) cells or precursors of CCR2+cells, and wherein the subject is not receiving an immune checkpoint inhibitor.

2. The method of claim 1, wherein the HSCs in the preparation are lineage depleted.

3. The method of claim 1, wherein the HSCs in the preparation are at least 10%, 20%, 30%, 40%, 50%, 60%, 70%, 80%, 90%, 95%, 98% or 99% CCR2+cells or precursors of CCR2+cells.

4. The method of claim 1, wherein the HSCs in the preparation are less than 50%, 40%, 30%, 20%, 10%, 5%, 2%, or less than 1% CCR2 negative (CCR2-) cells.

5. The method of claim 1, wherein between 50% and 100% of the cells in the preparation are CCR2+cells or precursors of CCR2+cells.

6. The method of claim 1, wherein the subject has been treated with radiation therapy or chemotherapy or wherein the subject is scheduled to receive radiation therapy or chemotherapy.

7. The method of claim 1, wherein the source of hematopoietic stem cells is bone marrow, peripheral blood, umbilical cord blood, or induced pluripotent stem cells.

8. The method of claim 1, wherein the source of hematopoietic stem cells is hematopoietic progenitor cells.

9. The method of claim 1, wherein the source of stem cells is autologous.

10. The method of claim 1, wherein the source of stem cells is allogeneic and the donor cells are HLA-matched to the recipient.

11. The method of claim 1, wherein the adoptive cell therapy comprises chimeric antibody receptor (CAR)-modified T cells.

12. The method of claim 1, wherein the disease is cancer and the cancer is melanoma, squamous cell carcinoma, basal cell carcinoma, breast cancer, head and neck carcinoma, thyroid carcinoma, soft tissue sarcoma, bone sarcoma, testicular cancer, prostatic cancer, ovarian cancer, bladder cancer, skin cancer, brain cancer, glioblastoma, medulloblastoma, ependymoma, angiosarcoma, hemangiosarcoma, mast cell tumor, primary hepatic cancer, small cell lung cancer, non-small-cell lung cancer, pancreatic cancer, gastrointestinal cancer, renal cell carcinoma, hematopoietic neoplasia, lymphoma, mesothelioma, glioblastoma, low-grade glioma, high-grade glioma, pediatric brain cancer, medulloblastoma, or a metastatic cancer thereof.

13. The method of claim 12, wherein the cancer is metastatic or refractory melanoma or a metastatic or refractory cancer of the brain, lung, or breast.

14. The method of claim 12, wherein the cancer is a metastatic brain cancer from non-small cell lung cancer, a metastatic brain cancer from melanoma, or a metastatic brain cancer from breast carcinoma.

15. The method of claim 12, wherein the cancer is glioblastoma, low-grade glioma, high-grade glioma, pediatric brain cancer, or medulloblastoma.

16. The method of claim 1, wherein the disease is an infectious disease.

17. The method of claim 16, wherein the infectious disease is (i) a chronic infectious disease, or (ii) a hepatitis, adenovirus, BK polyoma virus, human immunodeficiency virus (HIV), herpes simplex virus (HSY), respiratory syncytial virus (RSV), cytomegalovirus (CMV), Epstein-Barr vims (EBY), Influenza A, B, and/or C, vesicular stomatitis virus (VSV), vesicular stomatitis vims (VSV), *Staphylococcus* species including Methicillin-resistant *Staphylococcus aureus* (MRSA), or *Streptococcus* species including *Streptococcus pneumonia* infection, or a post-transplant infection.

18. The method of claim 17, wherein the infectious disease is Hepatitis A, Hepatitis B, or Hepatitis C.

19. An improvement in a method of treating a subject with adoptive cell therapy, the improvement comprising administering to the subject a preparation containing hematopoietic stem cells, wherein the hematopoietic stem cells (HSCs) are enriched for CCR2 positive (CCR2+) cells or precursors of CCR2+cells, and wherein the subject is not receiving an immune checkpoint inhibitor.

20. A kit comprising a package containing a first vessel containing T Cells for adoptive cell therapy and a second vessel containing hematopoietic stem cells (HSCs), wherein the HSCs are enriched for CCR2 positive (CCR2+) cells or precursors of CCR2+cells, and instructions for use wherein the instructions do not indicate use with an immune checkpoint inhibitor.

* * * * *